(12) United States Patent
Singh et al.

(10) Patent No.: US 8,716,477 B2
(45) Date of Patent: May 6, 2014

(54) CRYSTALLINE FORMS OF BOSENTAN SALTS AND PROCESSES FOR THEIR PREPARATION

(75) Inventors: Rakesh Singh, Jaunpur (IN); Anu Mittal, Kurukshetra (IN); Gopal Singh Bisht, New Delhi (IN); Mahavir Singh Khanna, New Delhi (IN); Rajesh Kumar Thaper, Jammu (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/509,125

(22) PCT Filed: Nov. 12, 2010

(86) PCT No.: PCT/IB2010/055153
§ 371 (c)(1), (2), (4) Date: Jul. 25, 2012

(87) PCT Pub. No.: WO2011/058524
PCT Pub. Date: May 19, 2011

(65) Prior Publication Data
US 2012/0283440 A1 Nov. 8, 2012

(30) Foreign Application Priority Data
Nov. 12, 2009 (IN) .......................... 2339/DEL/2009

(51) Int. Cl.
*C07D 403/04* (2006.01)
(52) U.S. Cl.
USPC .......................................... 544/296

(58) Field of Classification Search
USPC .......................................... 544/296
See application file for complete search history.

(56) References Cited

U.S. PATENT DOCUMENTS 5,292,740 A     3/1994   Burri et al. ................. 514/256
6,136,971 A   10/2000   Harrington et al. .......... 544/122

FOREIGN PATENT DOCUMENTS

| WO | WO 2008/135795 | 11/2008 | ......... C07D 403/04 |
| WO | WO 2009/047637 | 4/2009 | ......... C07D 403/04 |
| WO | WO 2009/083739 | 7/2009 | ......... C07D 239/69 |
| WO | WO 2009/093127 | 7/2009 | ......... C07D 403/04 |
| WO | WO 2009/095933 | 8/2009 | ......... C07D 401/04 |
| WO | WO 2010/103362 | 9/2010 | ......... C07D 239/52 |

*Primary Examiner* — Rebecca Anderson
*Assistant Examiner* — Karen Cheng

(57) ABSTRACT

The present invention relates to crystalline forms of bosentan salts and processes for their preparation.(FORMULA)

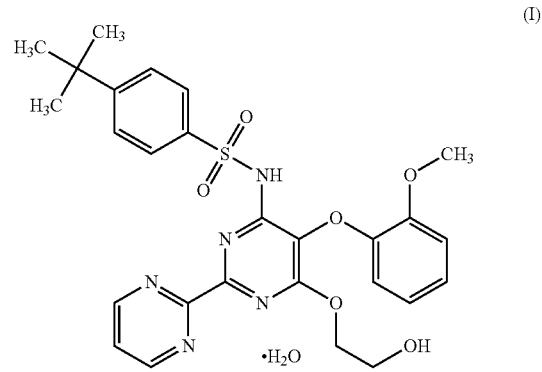

(I)

6 Claims, 24 Drawing Sheets

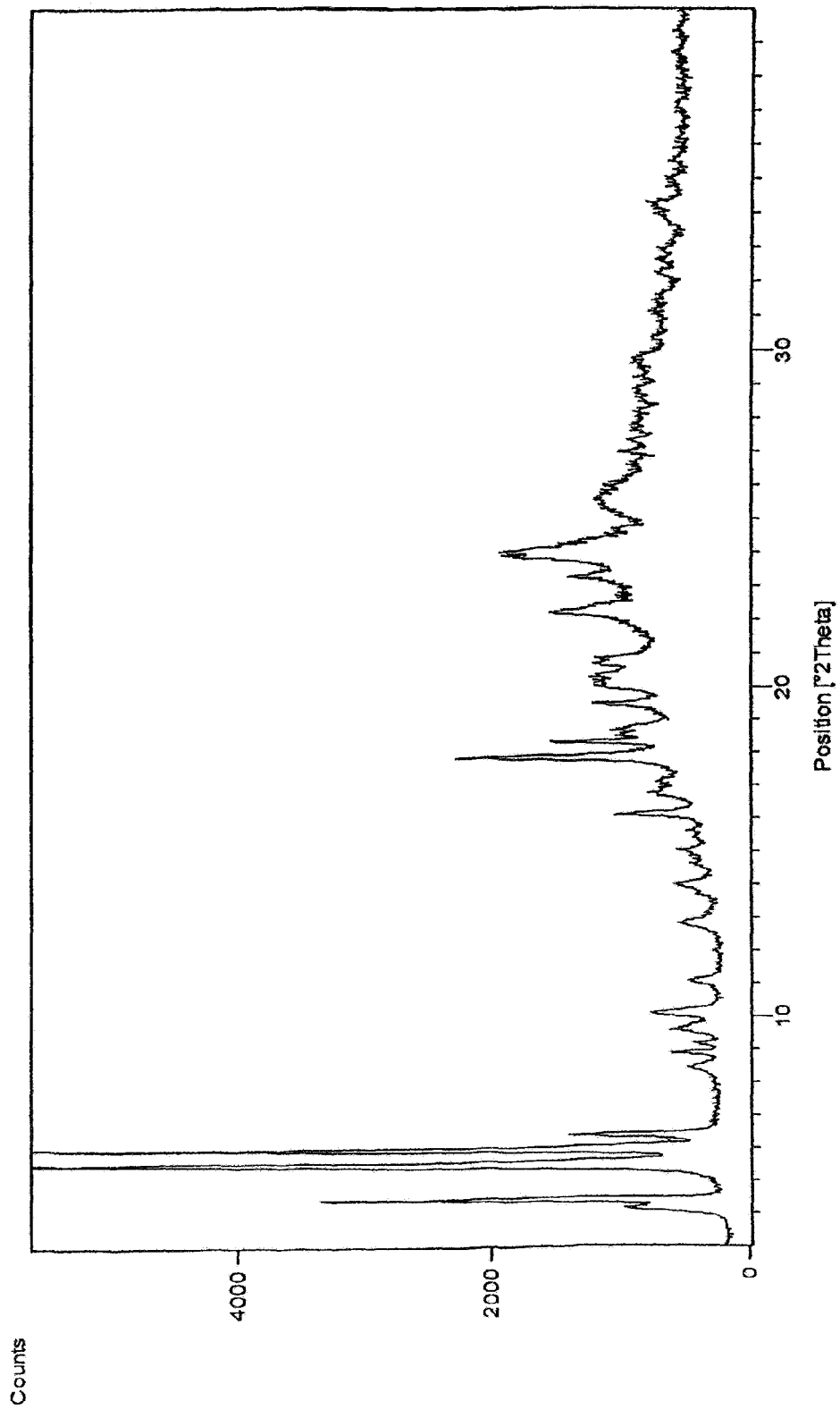

FIGURE 1A: THE TABLE OF VALUES FOR THE XRPD OF FIGURE 1.

| No. | Position [°2Th.] | d-spacing [Å] | Rel. Int. [%] |
|---|---|---|---|
| 1 | 4.10 | 21.54 | 13.09 |
| 2 | 4.44 | 19.89 | 57.66 |
| 3 | 5.53 | 15.97 | 100.00 |
| 4 | 5.99 | 14.76 | 99.89 |
| 5 | 6.42 | 13.78 | 21.74 |
| 6 | 10.12 | 8.74 | 10.33 |
| 7 | 16.12 | 5.49 | 14.07 |
| 8 | 16.74 | 5.29 | 8.17 |
| 9 | 17.87 | 4.96 | 36.03 |
| 10 | 18.33 | 4.84 | 21.99 |
| 11 | 18.72 | 4.74 | 12.58 |
| 12 | 19.49 | 4.55 | 16.35 |
| 13 | 20.01 | 4.44 | 14.83 |
| 14 | 20.85 | 4.26 | 15.13 |
| 15 | 22.20 | 4.00 | 21.22 |
| 16 | 23.26 | 3.82 | 18.39 |
| 17 | 23.83 | 3.73 | 26.00 |
| 18 | 24.02 | 3.70 | 27.09 |
| 19 | 26.97 | 3.31 | 10.04 |

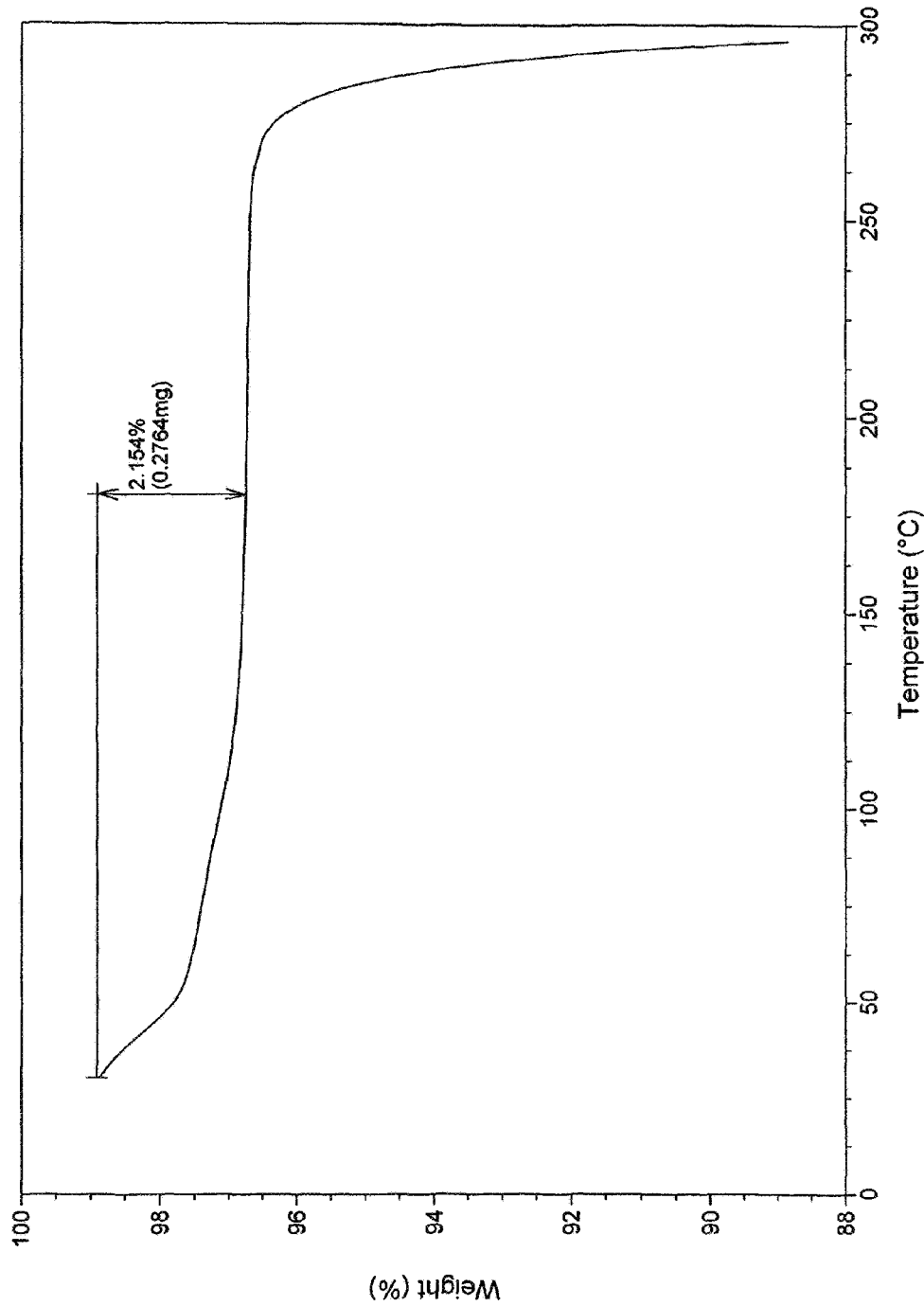

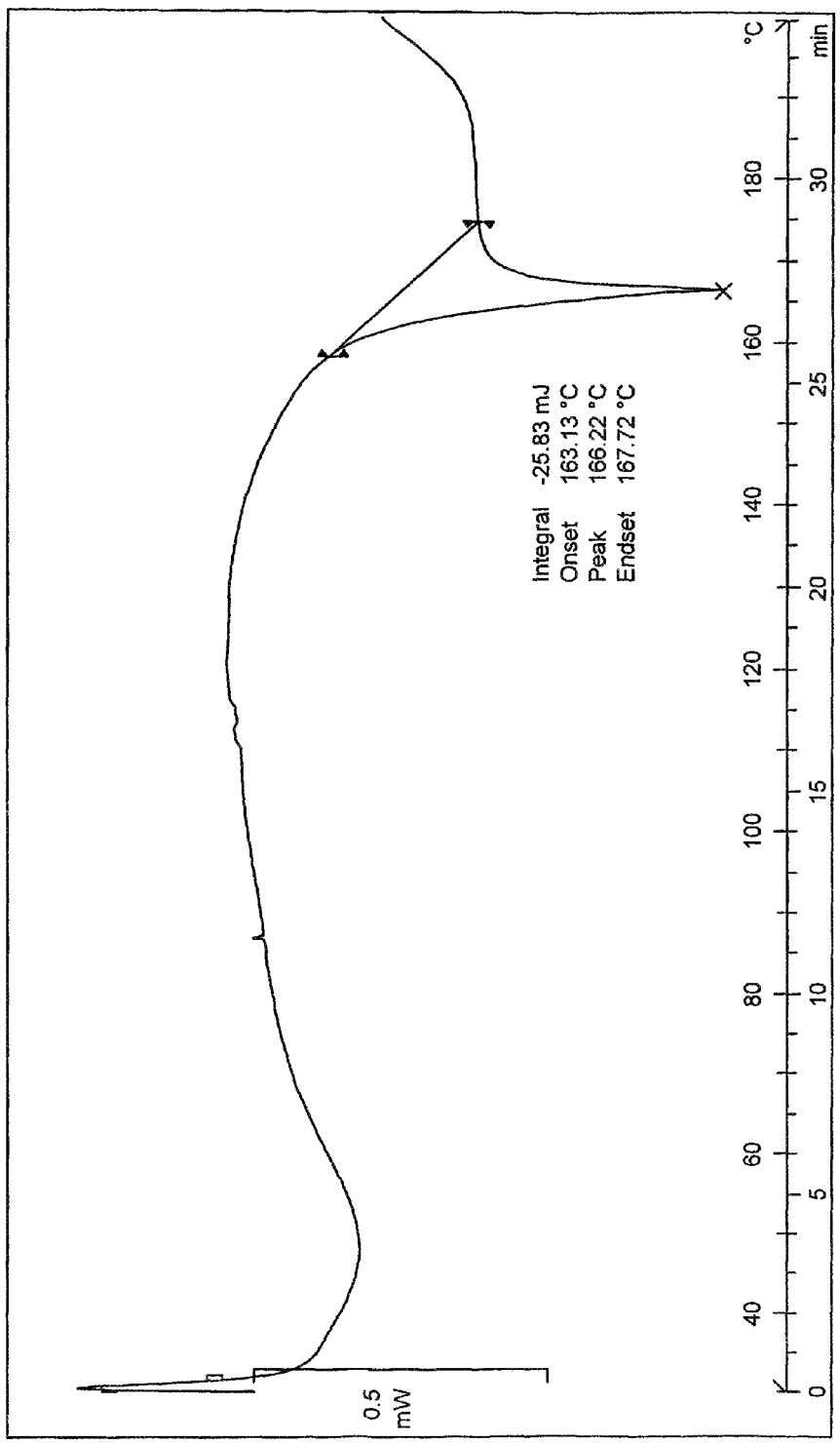
FIGURE 3: DIFFERENTIAL SCANNING CALORIMETRY OF FORM A OF BOSENTAN POTASSIUM

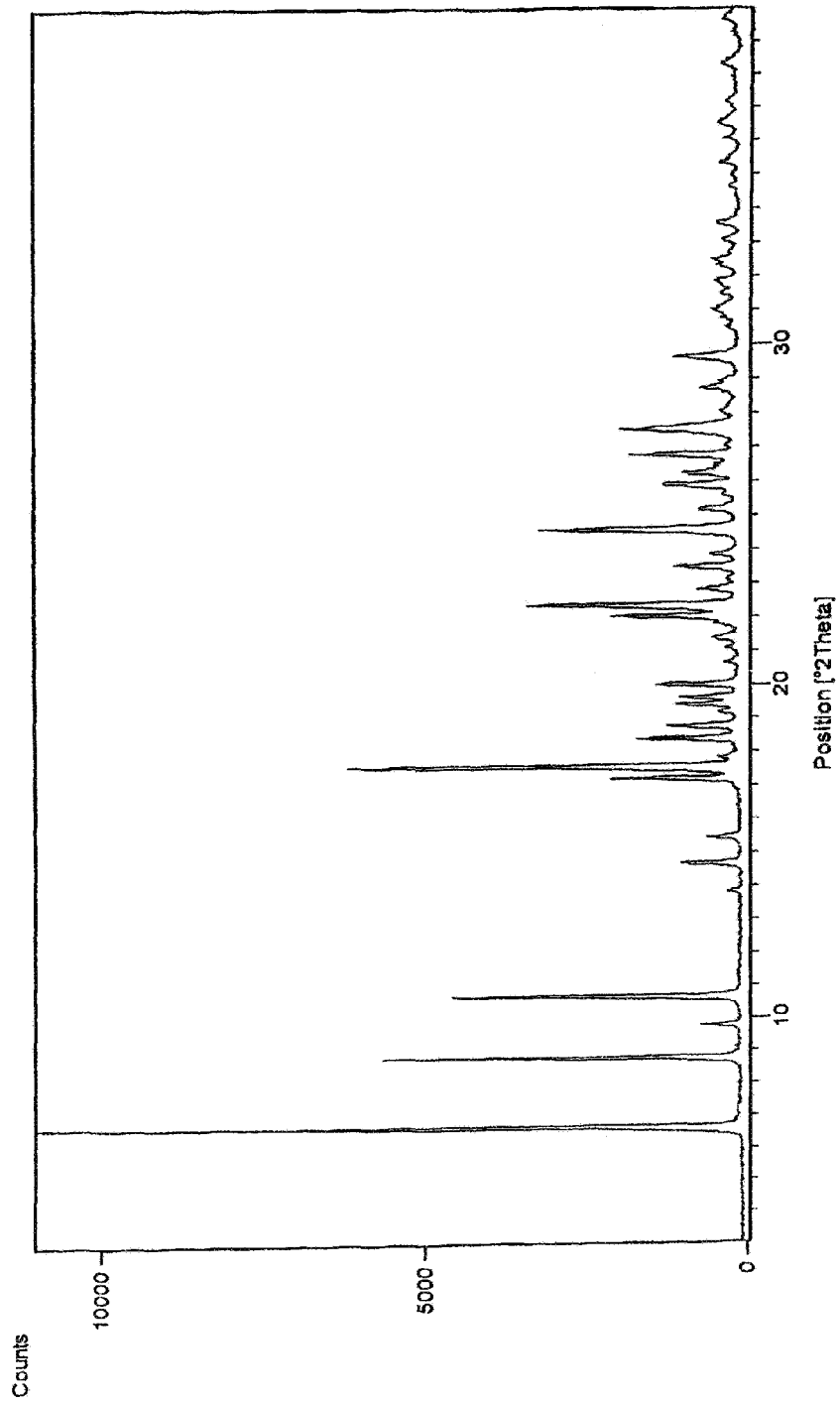
FIGURE 4: X-RAY DIFFRACTION PATTERN OF FORM B OF BOSENTAN POTASSIUM

FIGURE 4A: THE TABLE OF VALUES FOR THE XRPD OF FIGURE 4.

| No. | Position [°2Th.] | d-spacing [Å] | Rel. Int. [%] |
|---|---|---|---|
| 1 | 6.65 | 13.29 | 100.00 |
| 2 | 8.77 | 10.08 | 53.39 |
| 3 | 10.66 | 8.29 | 45.18 |
| 4 | 14.69 | 6.03 | 9.69 |
| 5 | 17.19 | 5.16 | 20.33 |
| 6 | 17.56 | 5.05 | 63.01 |
| 7 | 18.39 | 4.82 | 16.21 |
| 8 | 18.76 | 4.73 | 11.69 |
| 9 | 19.40 | 4.57 | 9.85 |
| 10 | 19.60 | 4.53 | 9.50 |
| 11 | 19.98 | 4.44 | 13.08 |
| 12 | 21.99 | 4.04 | 20.41 |
| 13 | 22.32 | 3.98 | 34.53 |
| 14 | 23.46 | 3.79 | 10.70 |
| 15 | 24.53 | 3.63 | 32.83 |
| 16 | 25.88 | 3.44 | 12.24 |
| 17 | 26.19 | 3.40 | 9.44 |
| 18 | 26.73 | 3.33 | 17.82 |
| 19 | 27.47 | 3.25 | 19.20 |
| 20 | 28.72 | 3.11 | 6.68 |
| 21 | 29.60 | 3.02 | 10.67 |

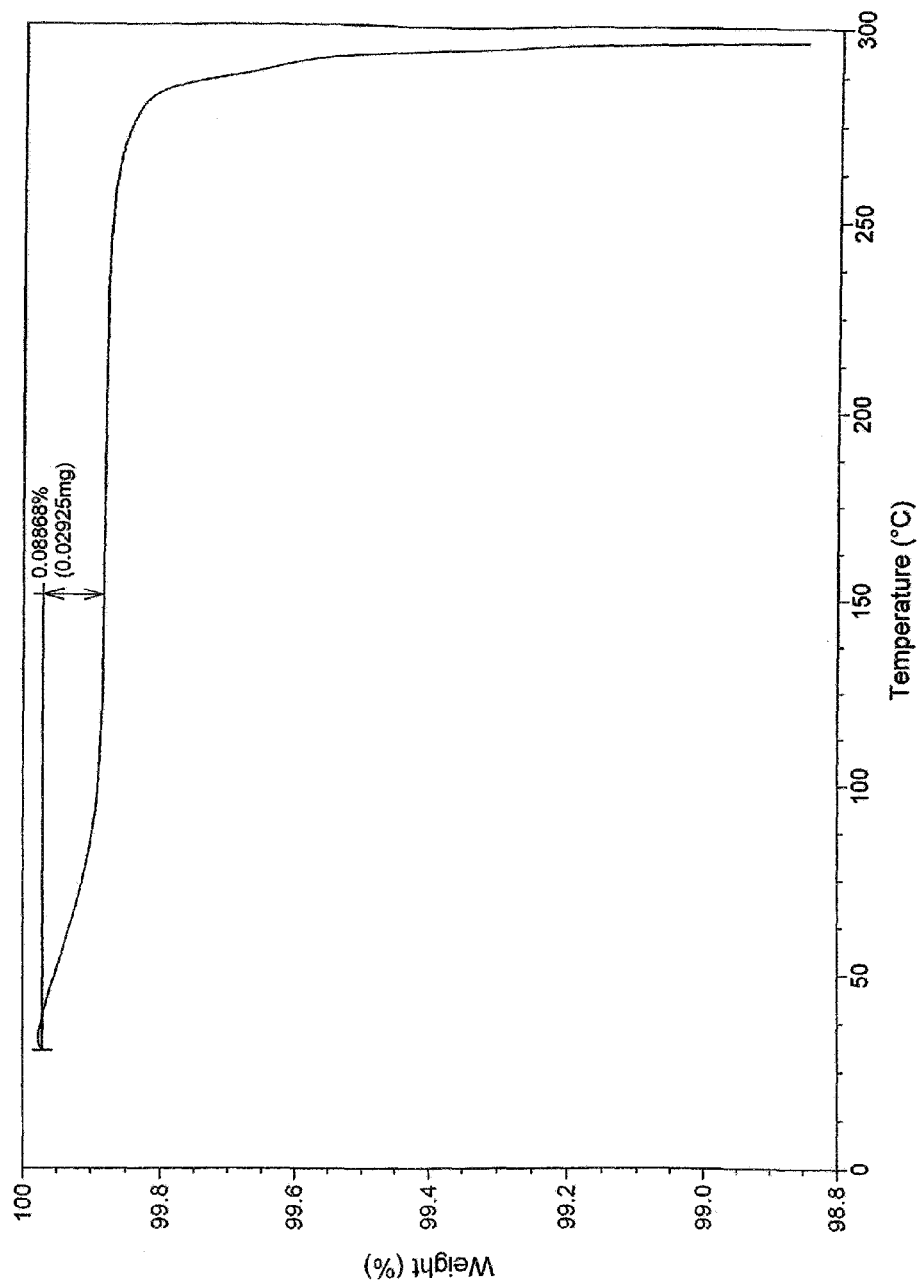

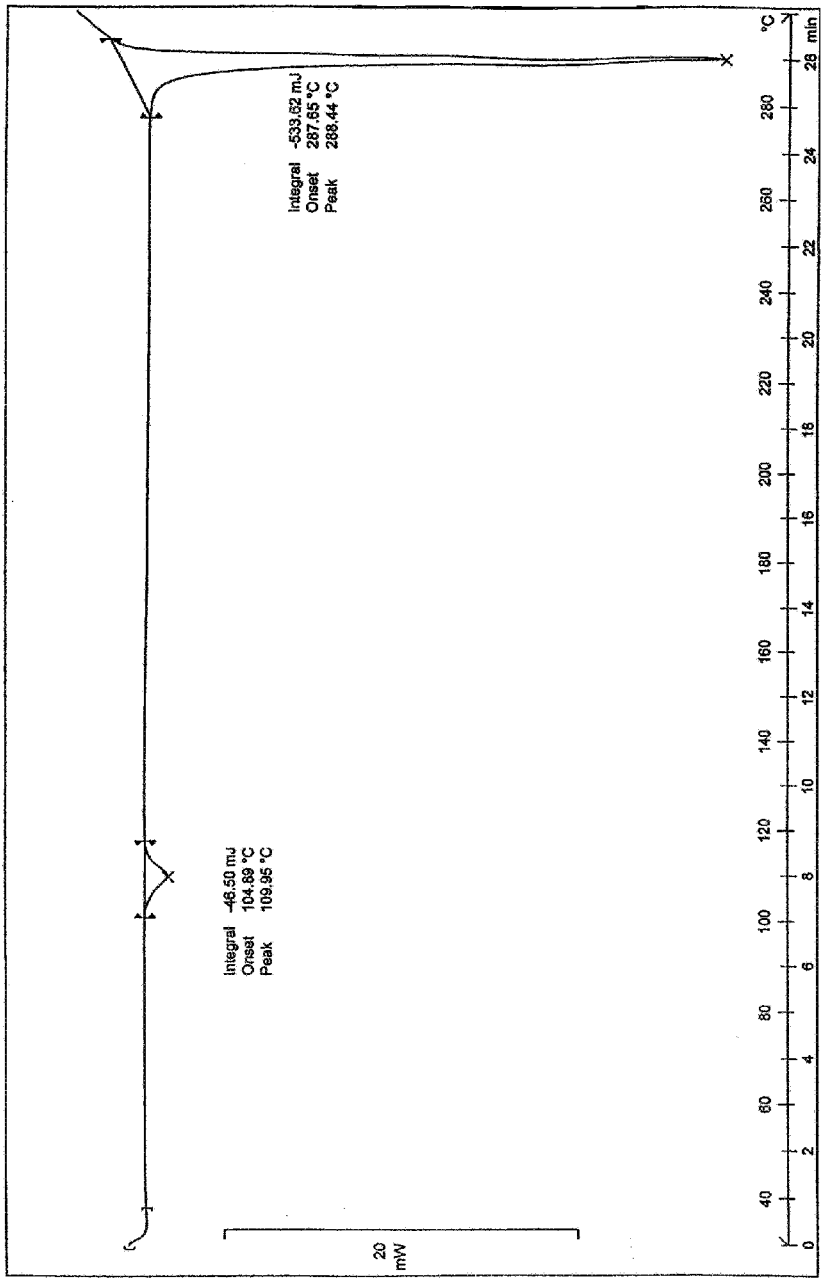

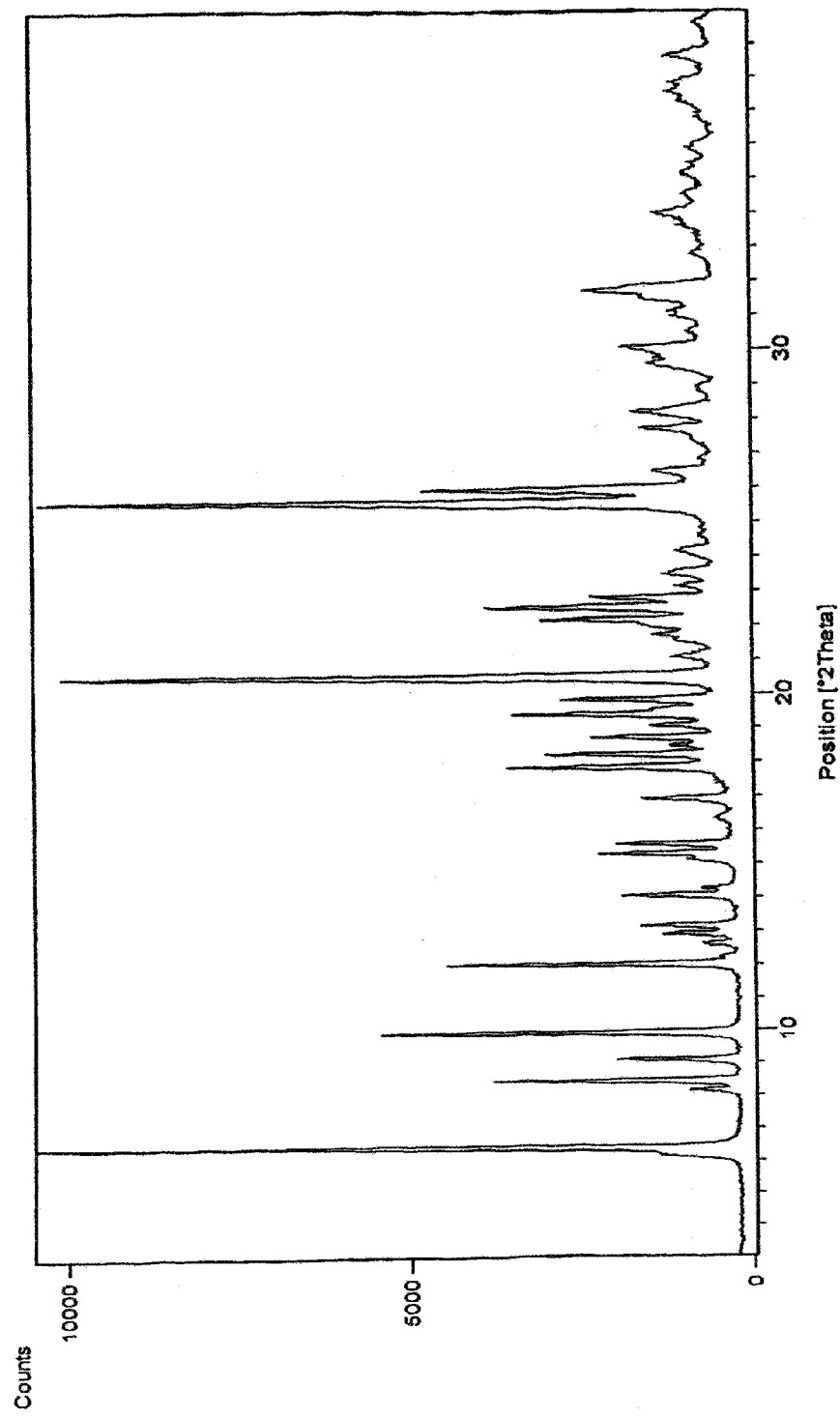

FIGURE 7A: THE TABLE OF VALUES FOR THE XRPD OF FIGURE 7

| No. | Position [°2Th.] | d-spacing [Å] | Rel. Int. [%] |
|---|---|---|---|
| 1 | 6.18 | 14.29 | 11.87 |
| 2 | 6.45 | 13.07 | 92.51 |
| 4 | 8.45 | 10.47 | 33.32 |
| 5 | 9.09 | 9.73 | 17.08 |
| 6 | 9.94 | 8.90 | 49.92 |
| 7 | 12.02 | 7.36 | 39.68 |
| 8 | 12.92 | 6.85 | 10.32 |
| 9 | 13.17 | 6.72 | 13.65 |
| 10 | 14.07 | 6.29 | 16.29 |
| 11 | 15.31 | 5.79 | 19.05 |
| 12 | 15.59 | 5.68 | 16.67 |
| 13 | 16.92 | 5.24 | 12.99 |
| 14 | 17.84 | 4.97 | 31.55 |
| 15 | 18.21 | 4.87 | 25.56 |
| 16 | 18.47 | 4.80 | 9.21 |
| 17 | 18.71 | 4.74 | 20.66 |
| 18 | 19.06 | 4.66 | 11.23 |
| 19 | 19.38 | 4.58 | 30.57 |
| 20 | 19.82 | 4.48 | 23.51 |
| 21 | 20.48 | 4.34 | 95.10 |
| 22 | 21.04 | 4.22 | 8.23 |
| 24 | 21.69 | 4.10 | 10.93 |
| 25 | 22.13 | 4.01 | 27.23 |
| 26 | 22.47 | 3.95 | 34.61 |
| 27 | 22.76 | 3.90 | 19.76 |
| 29 | 23.45 | 3.79 | 8.91 |
| 31 | 25.55 | 3.48 | 100.00 |
| 32 | 25.92 | 3.43 | 43.11 |
| 33 | 26.49 | 3.36 | 9.49 |
| 34 | 27.71 | 3.22 | 11.56 |
| 35 | 28.19 | 3.16 | 12.91 |
| 36 | 29.58 | 3.02 | 10.06 |
| 37 | 30.07 | 2.97 | 13.56 |
| 38 | 31.01 | 2.88 | 6.18 |
| 39 | 31.68 | 2.82 | 19.95 |
| 40 | 33.97 | 2.64 | 9.02 |

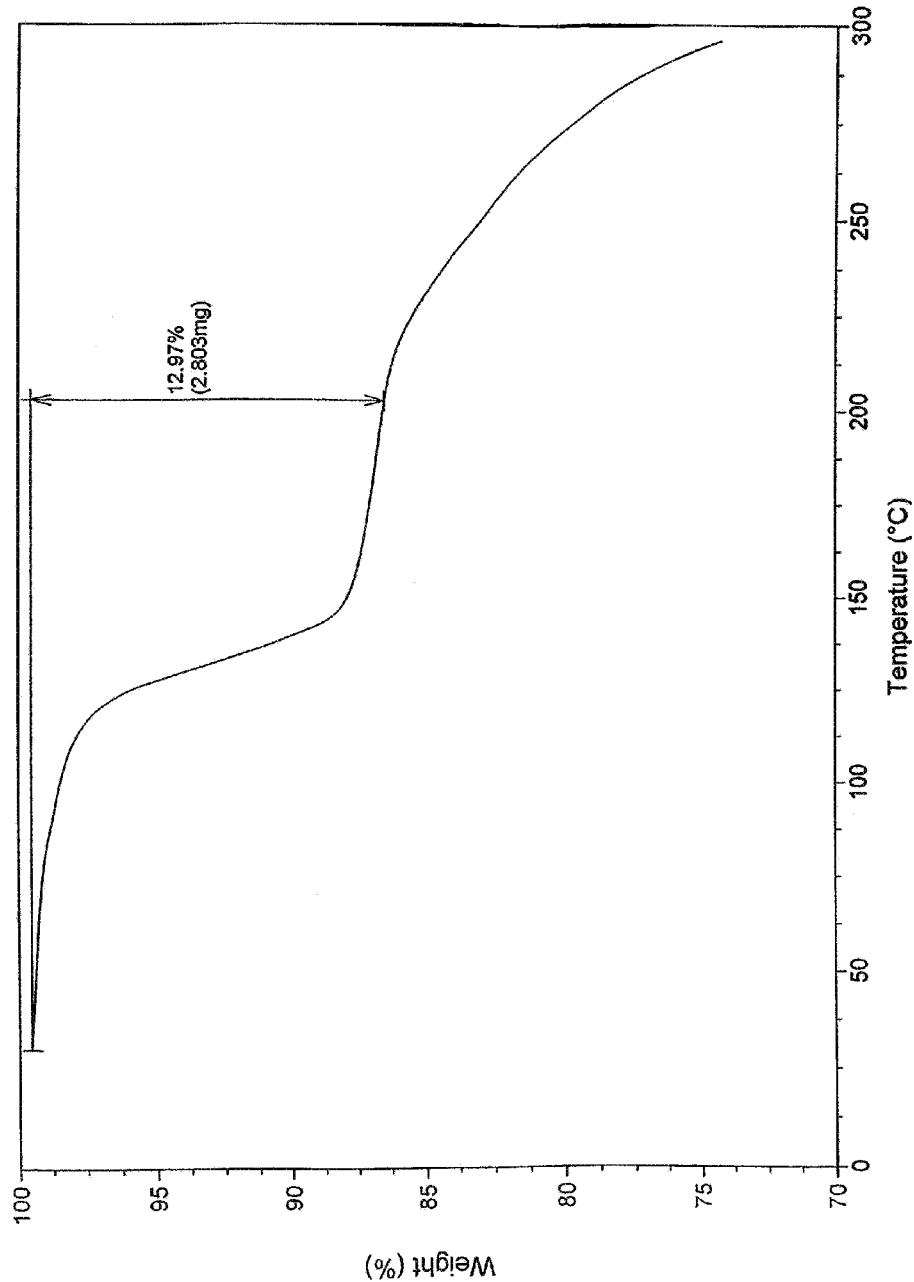
FIGURE 8: THERMAL GRAVIMETRIC ANALYSIS OF FORM C OF BOSENTAN SODIUM

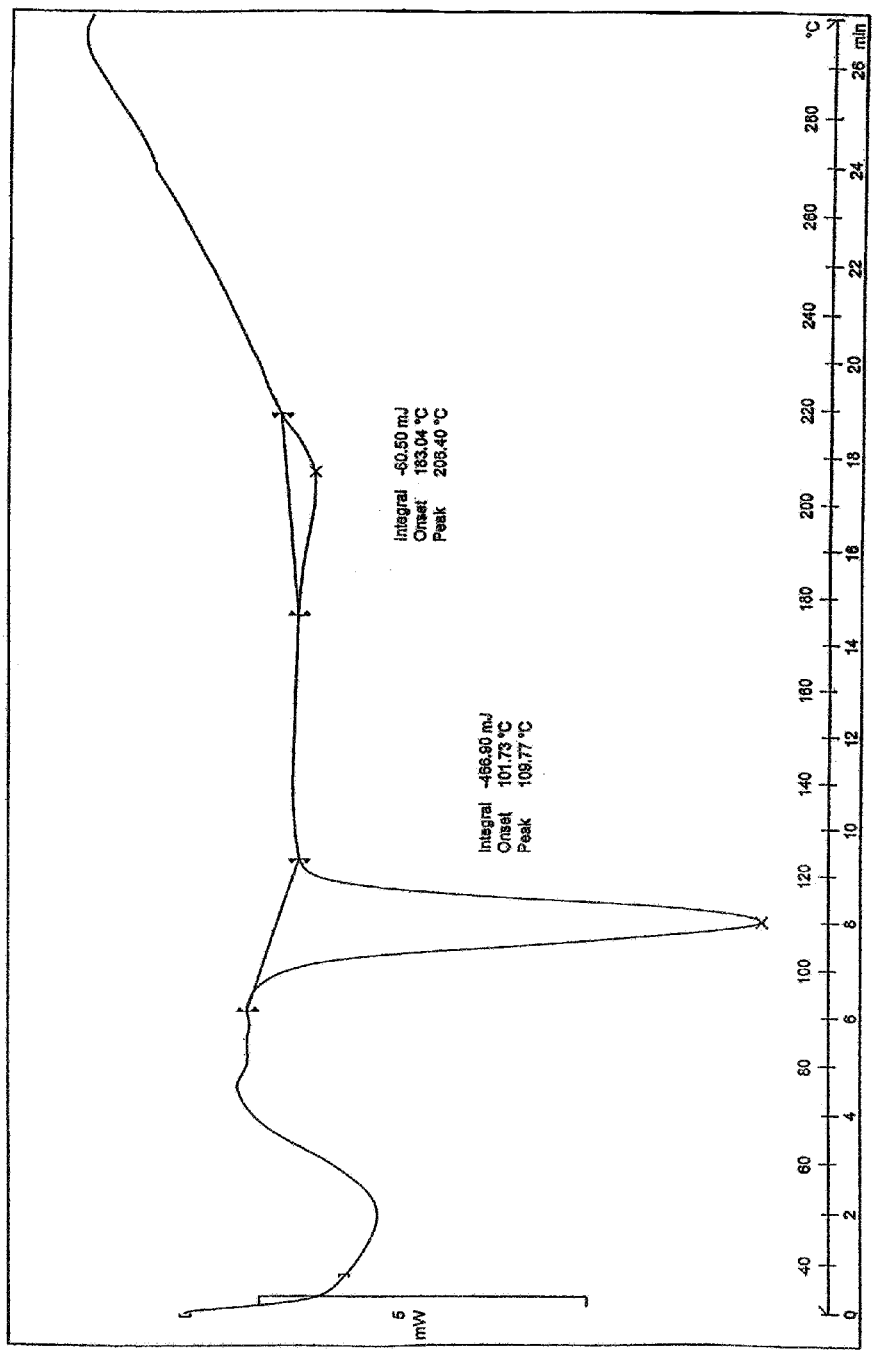
FIGURE 9: DIFFERENTIAL SCANNING CALORIMETRY OF FORM C OF BOSENTAN SODIUM

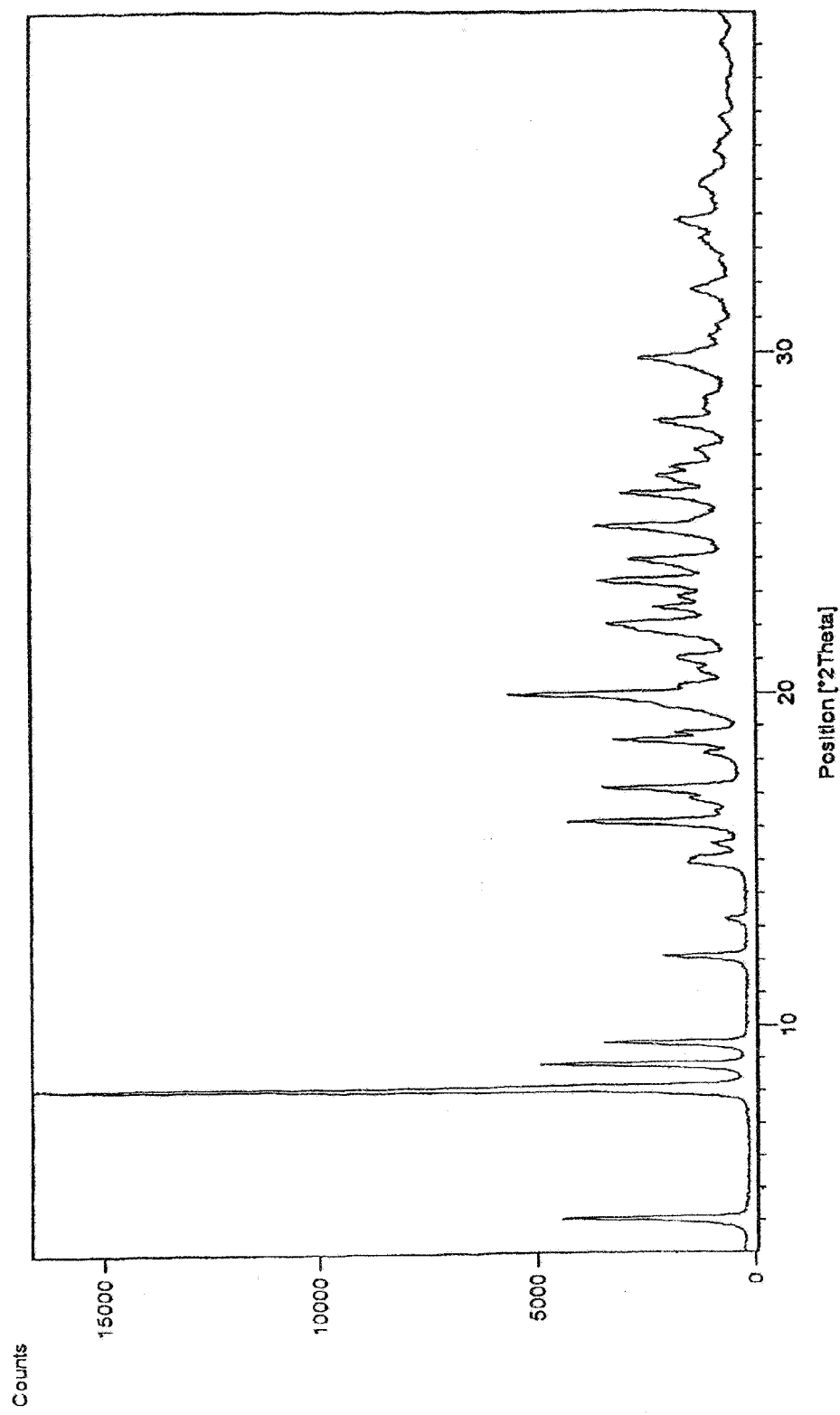
FIGURE 10: X-RAY DIFFRACTION PATTERN OF FORM D OF BOSENTAN SODIUM

FIGURE 10A: THE TABLE OF VALUES FOR THE XRPD OF FIGURE 10

| No. | Position [°2Th.] | d-spacing [Å] | Rel. Int. [%] |
|---|---|---|---|
| 1 | 4.06 | 21.77 | 26.13 |
| 2 | 8.09 | 10.94 | 100.00 |
| 3 | 8.80 | 10.05 | 29.35 |
| 4 | 9.47 | 9.34 | 20.12 |
| 5 | 12.12 | 7.30 | 12.17 |
| 6 | 14.89 | 5.95 | 8.68 |
| 7 | 15.11 | 5.86 | 7.69 |
| 8 | 16.18 | 5.48 | 25.61 |
| 9 | 16.82 | 5.27 | 8.17 |
| 10 | 17.16 | 5.17 | 20.58 |
| 11 | 18.59 | 4.77 | 19.05 |
| 12 | 18.80 | 4.72 | 10.37 |
| 13 | 19.55 | 4.54 | 12.13 |
| 14 | 19.94 | 4.45 | 34.14 |
| 15 | 20.24 | 4.39 | 9.31 |
| 16 | 21.07 | 4.22 | 9.55 |
| 17 | 21.79 | 4.08 | 15.85 |
| 18 | 22.03 | 4.04 | 20.31 |
| 19 | 22.51 | 3.95 | 13.73 |
| 20 | 22.86 | 3.89 | 9.87 |
| 21 | 23.30 | 3.82 | 21.47 |
| 22 | 23.92 | 3.72 | 17.43 |
| 23 | 24.90 | 3.58 | 21.81 |
| 24 | 25.86 | 3.45 | 18.53 |
| 25 | 26.36 | 3.38 | 13.58 |
| 26 | 26.66 | 3.34 | 10.77 |
| 27 | 27.12 | 3.29 | 7.35 |
| 28 | 28.01 | 3.19 | 13.01 |
| 29 | 29.79 | 2.99 | 15.93 |
| 30 | 31.81 | 2.81 | 8.03 |
| 31 | 33.83 | 2.65 | 10.27 |
| 32 | 34.81 | 2.58 | 7.03 |

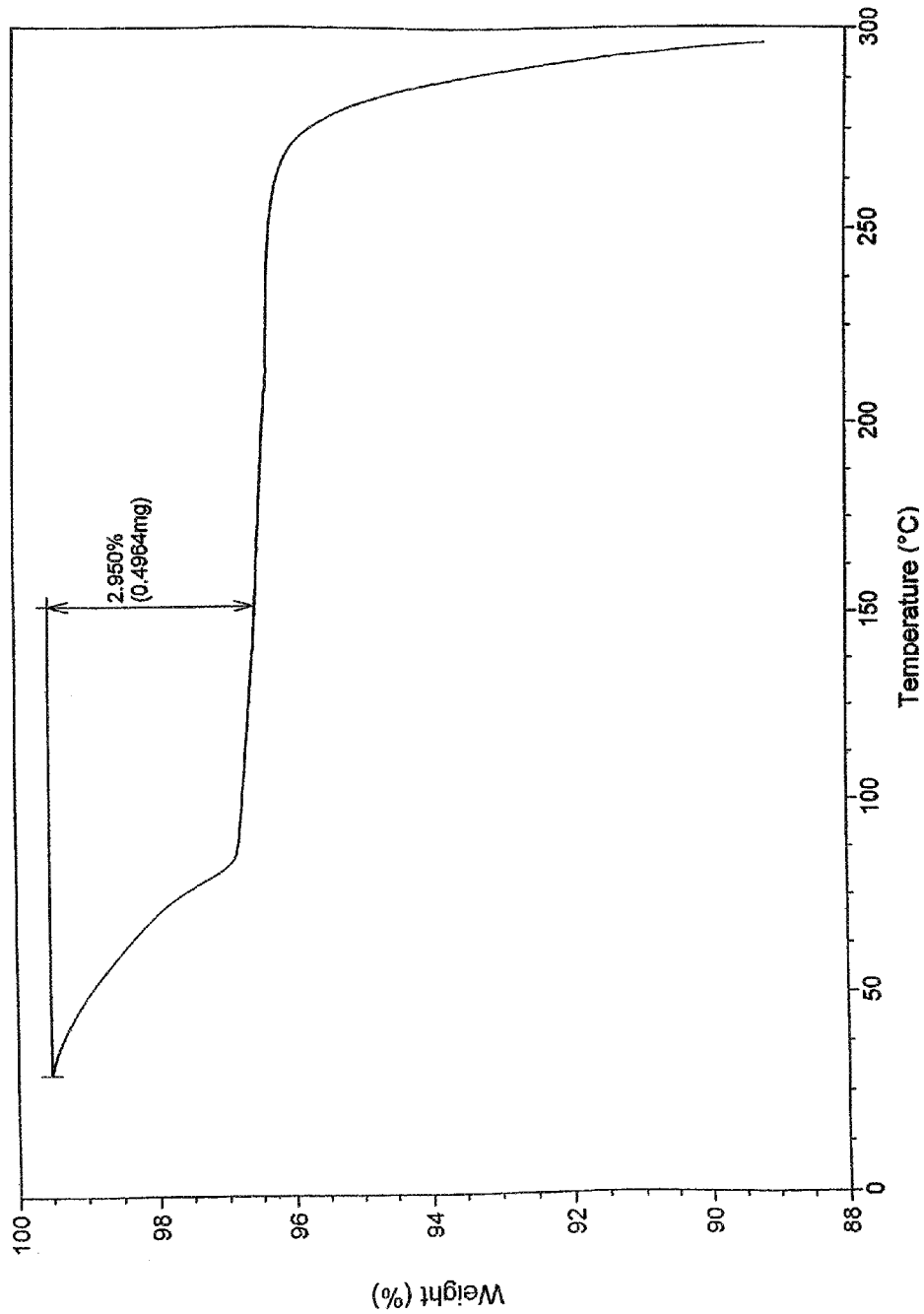

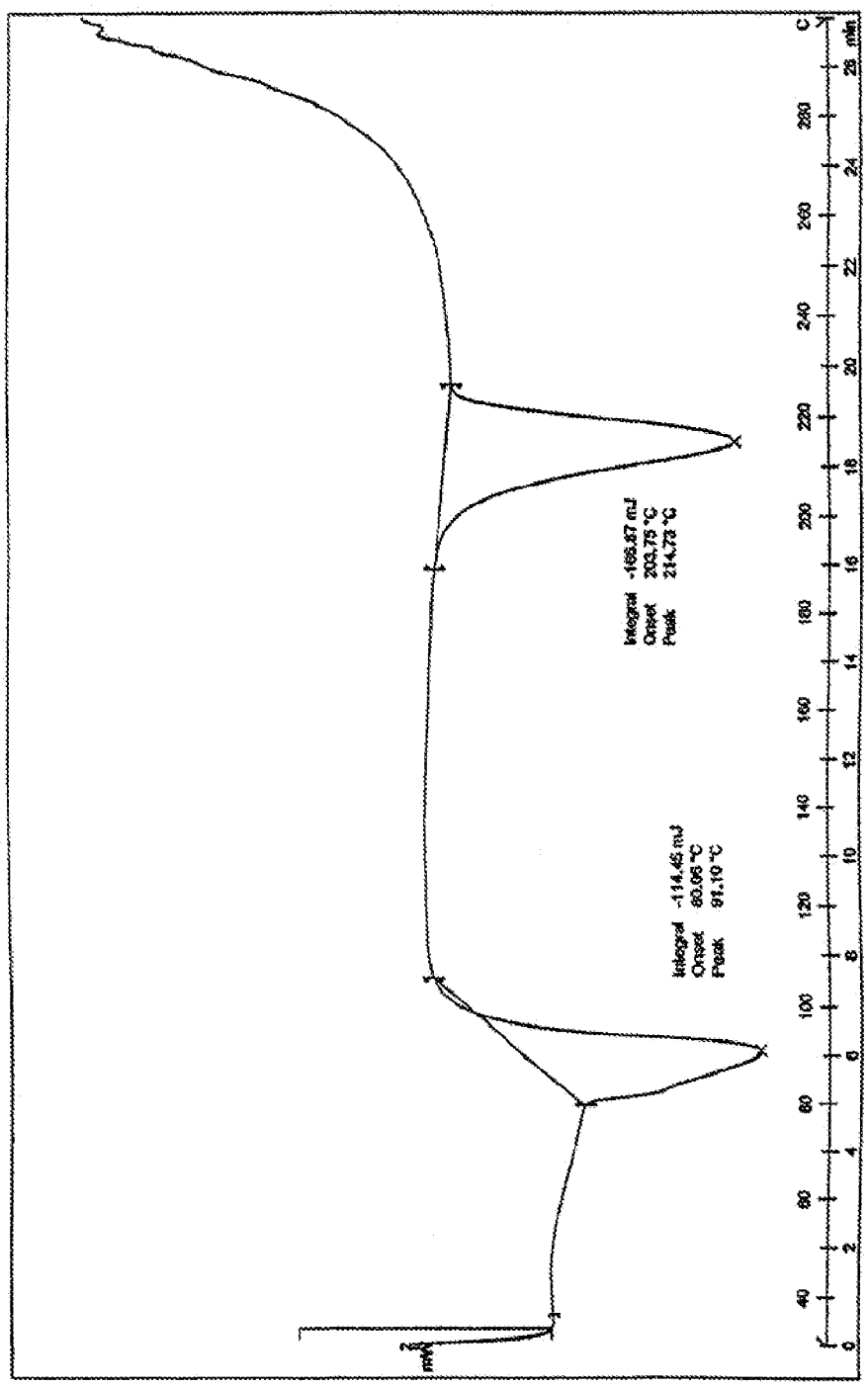
FIGURE 12: DIFFERENTIAL SCANNING CALORIMETRY OF FORM D OF BOSENTAN SODIUM

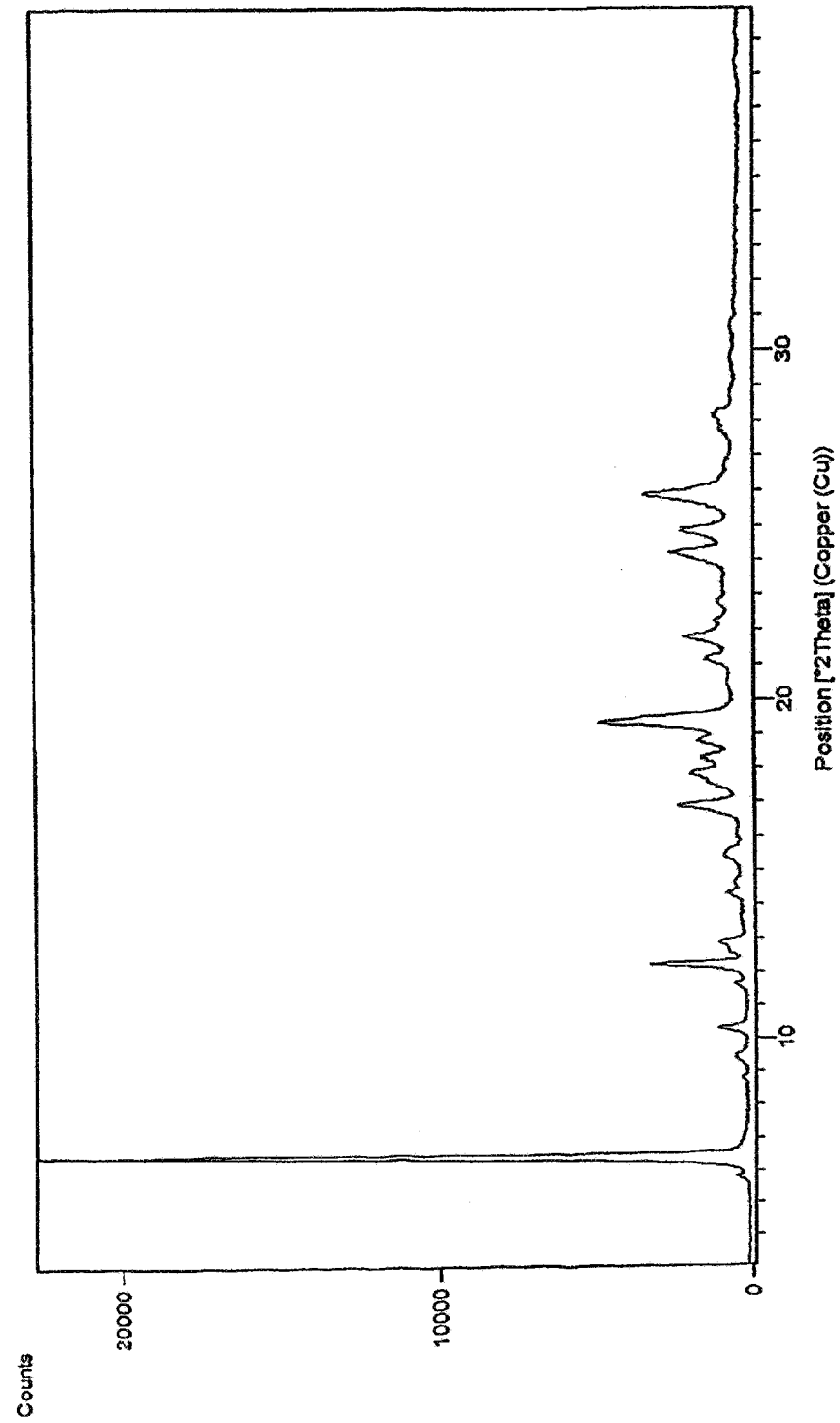
FIGURE 13: X-RAY DIFFRACTION PATTERN OF FORM E OF BOSENTAN AMMONIUM

FIGURE 13A: THE TABLE OF VALUES FOR THE XRPD OF FIGURE 13.

| No. | Position [°2Th.] | d-spacing [Å] | Rel. Int. [%] |
|---|---|---|---|
| 1 | 6.45 | 13.69 | 100.00 |
| 2 | 12.25 | 7.22 | 13.81 |
| 3 | 15.39 | 5.76 | 7.14 |
| 4 | 16.91 | 5.24 | 10.70 |
| 5 | 17.89 | 4.96 | 8.13 |
| 6 | 18.78 | 4.72 | 9.65 |
| 7 | 19.31 | 4.59 | 20.57 |
| 8 | 19.50 | 4.55 | 12.34 |
| 9 | 21.16 | 4.19 | 7.38 |
| 10 | 21.77 | 4.08 | 7.17 |
| 11 | 24.19 | 3.68 | 9.94 |
| 12 | 24.84 | 3.58 | 12.35 |
| 13 | 25.83 | 3.44 | 19.65 |

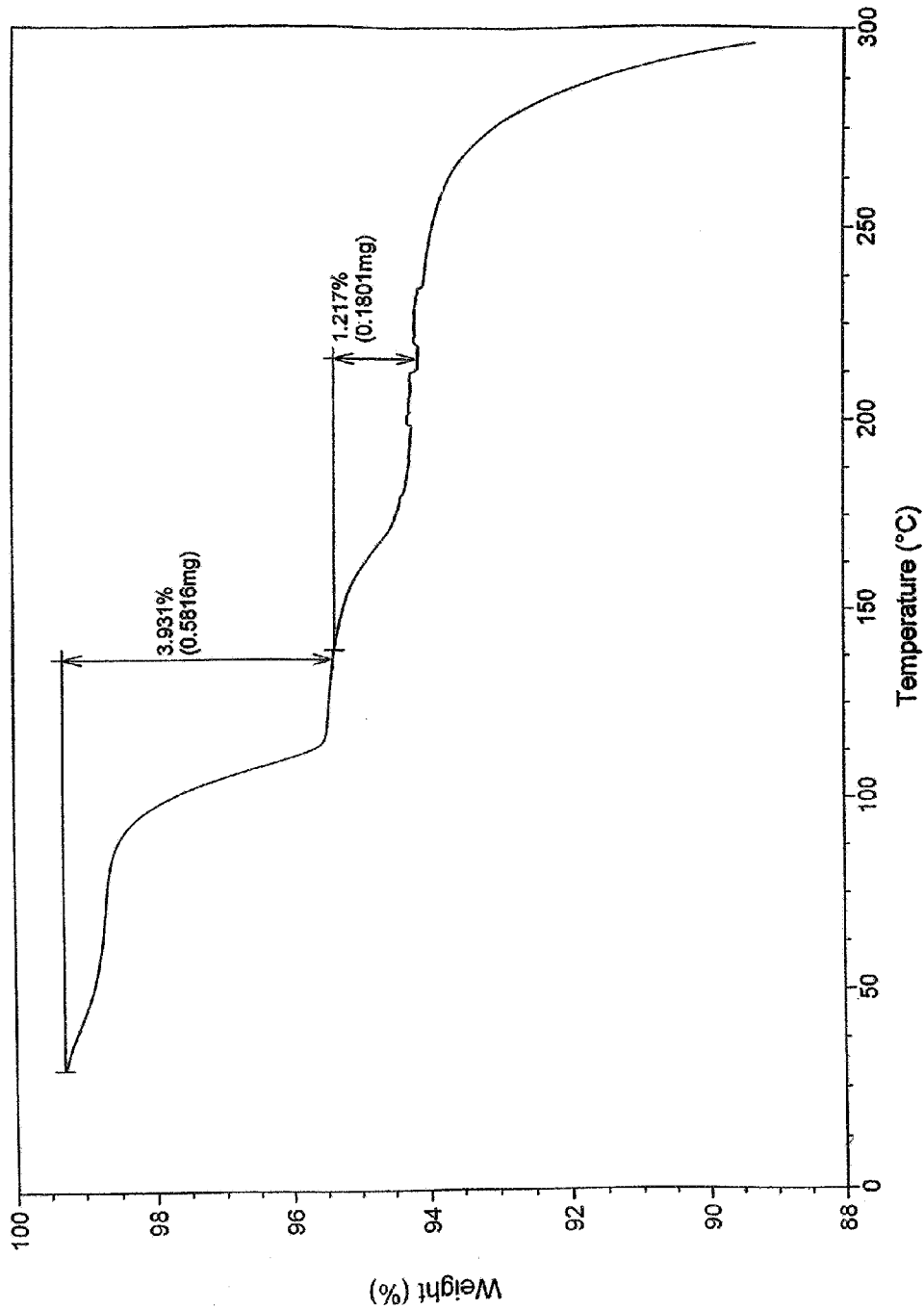

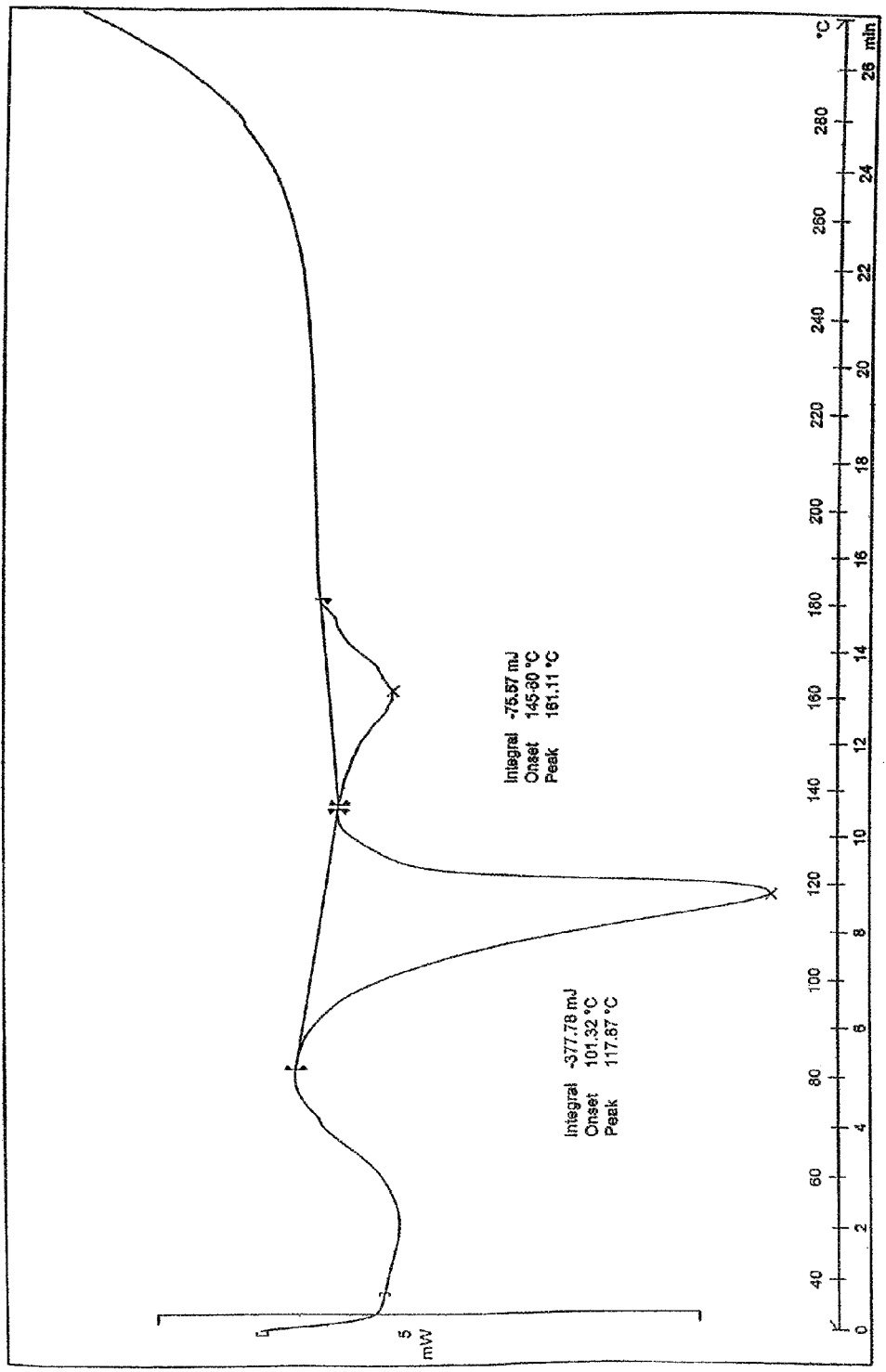
FIGURE 15: DIFFERENTIAL SCANNING CALORIMETRY OF FORM E OF BOSENTAN AMMONIUM

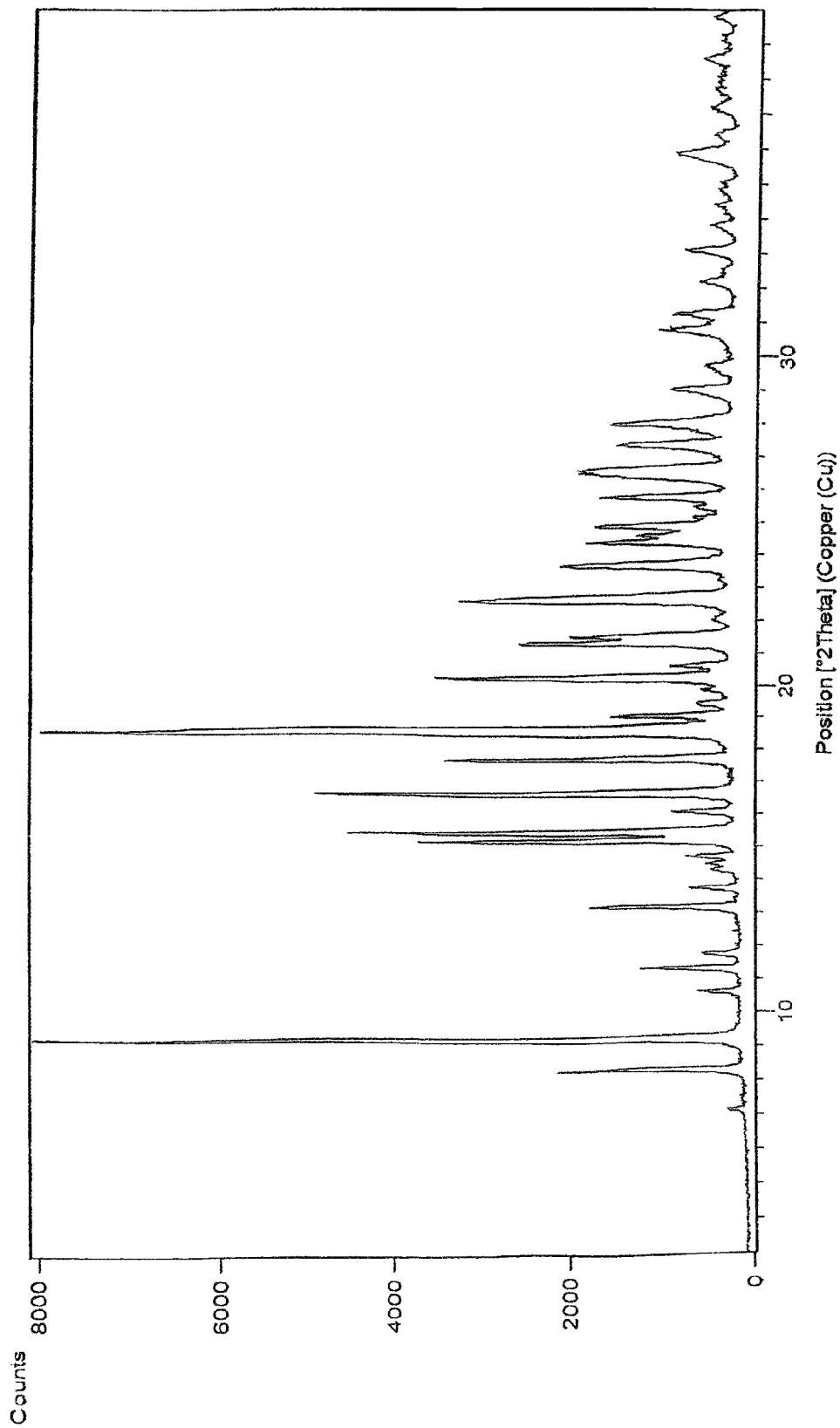
FIGURE 16: X-RAY DIFFRACTION PATTERN OF FORM F OF BOSENTAN AMMONIUM

FIGURE 16A: THE TABLE OF VALUES FOR THE XRPD OF FIGURE 16.

| No. | Position [°2Th.] | d-spacing [Å] | Rel. Int. [%] |
|---|---|---|---|
| 1 | 8.32 | 10.63 | 24.68 |
| 2 | 9.24 | 9.57 | 94.60 |
| 3 | 11.31 | 7.82 | 13.43 |
| 4 | 13.18 | 6.72 | 19.72 |
| 5 | 15.23 | 5.82 | 43.65 |
| 6 | 15.49 | 5.72 | 72.47 |
| 7 | 16.09 | 5.51 | 10.32 |
| 8 | 16.68 | 5.32 | 71.16 |
| 9 | 17.73 | 5.00 | 40.67 |
| 10 | 18.57 | 4.78 | 100.00 |
| 11 | 18.71 | 4.74 | 60.02 |
| 12 | 19.06 | 4.66 | 17.33 |
| 13 | 19.46 | 4.56 | 7.82 |
| 14 | 20.27 | 4.38 | 76.72 |
| 15 | 20.59 | 4.31 | 10.51 |
| 16 | 21.30 | 4.17 | 36.09 |
| 17 | 21.53 | 4.13 | 21.89 |
| 18 | 22.59 | 3.94 | 38.28 |
| 19 | 22.73 | 3.91 | 30.23 |
| 20 | 23.69 | 3.76 | 45.52 |
| 21 | 24.37 | 3.65 | 20.81 |
| 22 | 24.85 | 3.58 | 26.52 |
| 23 | 25.75 | 3.46 | 27.88 |
| 24 | 26.31 | 3.39 | 17.56 |
| 25 | 26.63 | 3.35 | 29.29 |
| 26 | 27.39 | 3.26 | 30.64 |
| 27 | 27.96 | 3.19 | 20.32 |
| 28 | 29.00 | 3.08 | 10.29 |
| 29 | 30.73 | 2.91 | 10.73 |
| 30 | 31.21 | 2.87 | 10.76 |
| 31 | 33.07 | 2.71 | 7.36 |
| 32 | 35.84 | 2.51 | 10.02 |

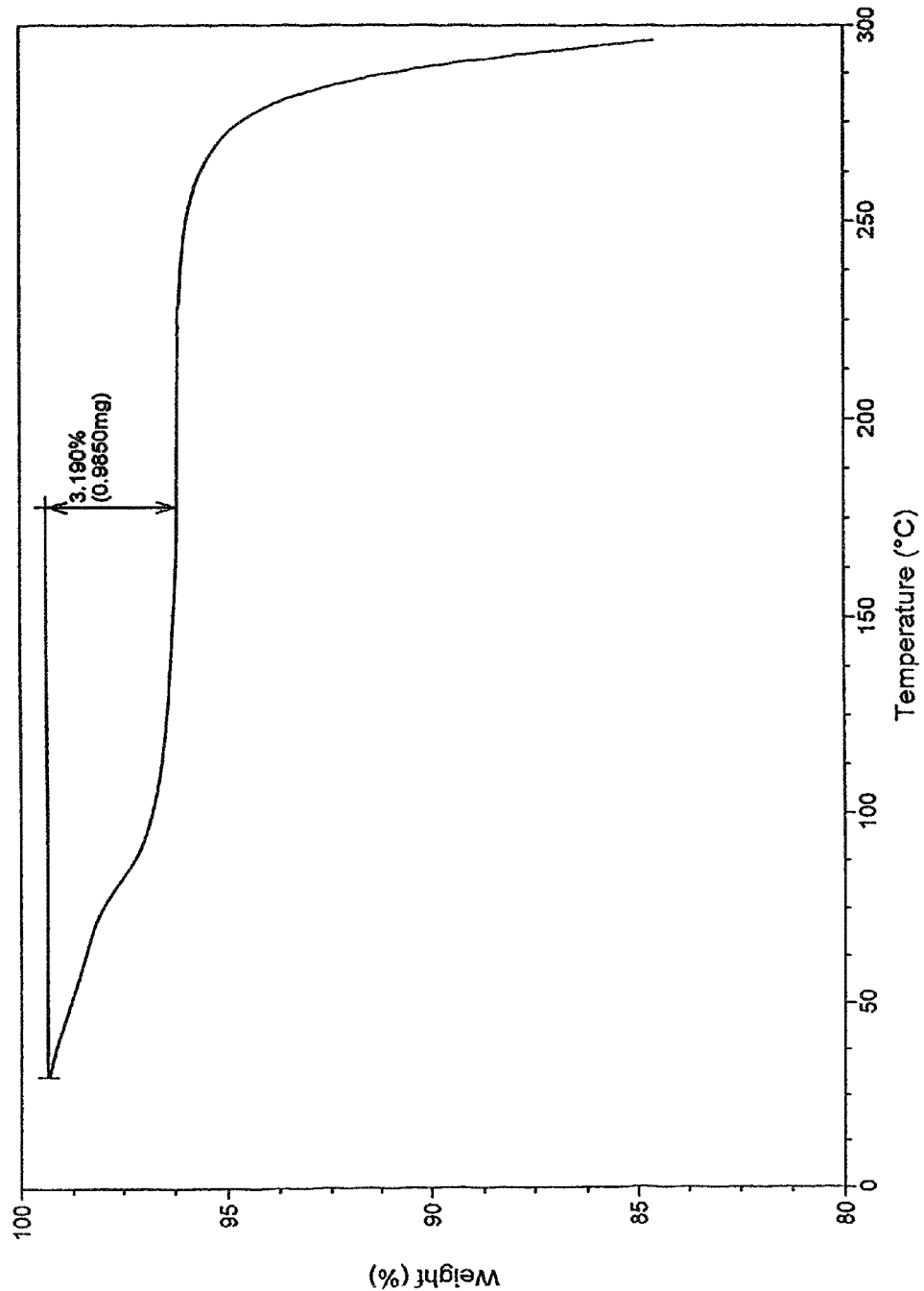

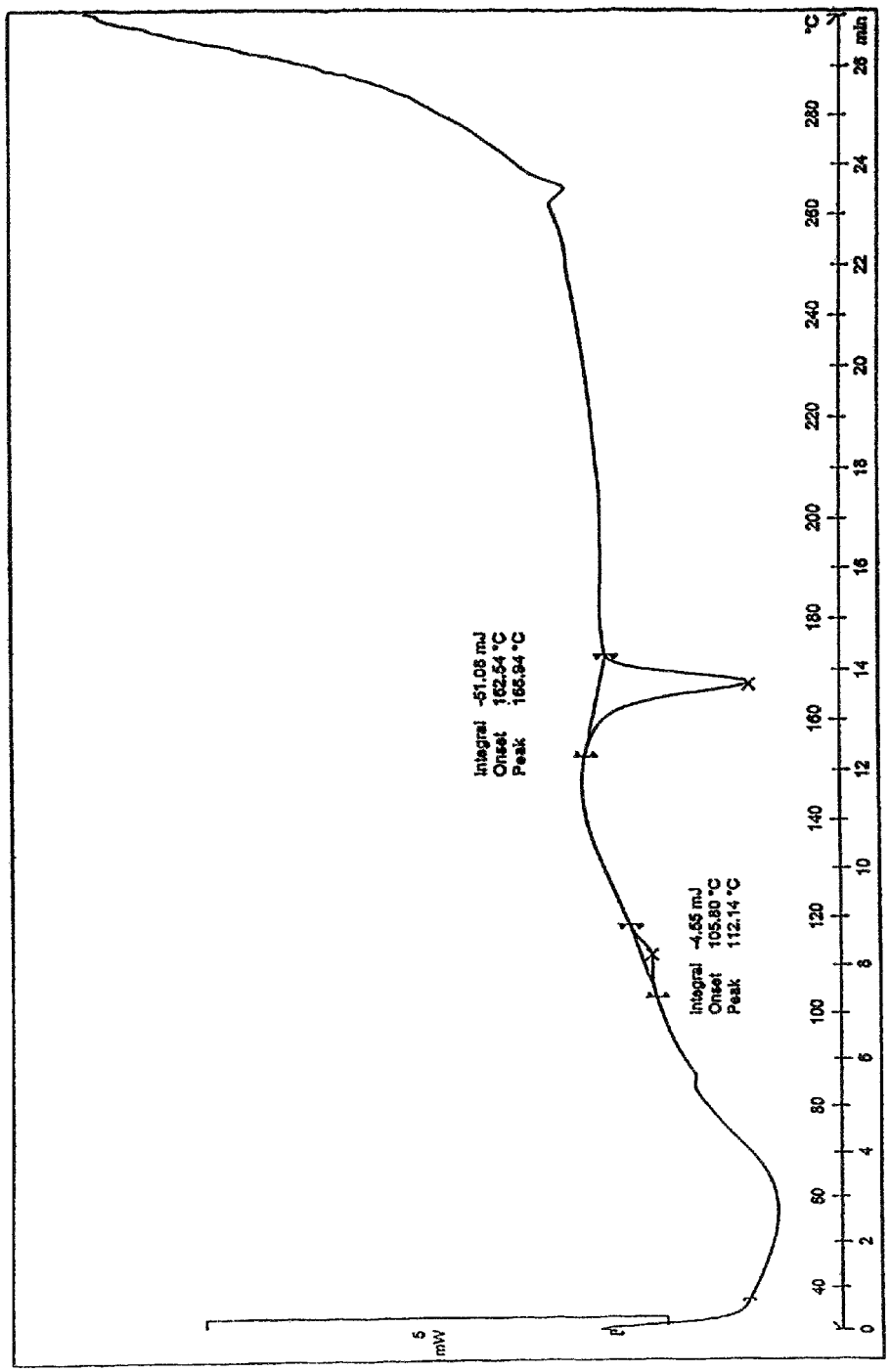

CRYSTALLINE FORMS OF BOSENTAN SALTS AND PROCESSES FOR THEIR PREPARATION

CROSS-REFERENCE TO RELATED APPLICATION

This application is the national phase under 35 U.S.C. 371 of International Application No. PCT/IB2010/055153, filed on Nov. 12, 2010, which claims the benefit of foreign priority under 35 U.S.C. 119 to Indian Publication No. 2339/DEL/2009, filed on Nov. 12 2009.

FIELD OF THE INVENTION

The present invention relates to crystalline forms of bosentan salts and processes for their preparation.

BACKGROUND OF THE INVENTION

Bosentan is an endothelin receptor antagonist, belonging to a class of highly substituted pyrimidine derivatives. Bosentan is marketed in its monohydrate form chemically known as 4-tert-butyl-N-[6-(2-hydroxy-ethoxy)-5-(2-methoxy-phenoxy)-[2,2']-bipyrimidin-4-yl]-benzene sulfonamide monohydrate, which is represented by Formula 1.

Formula 1

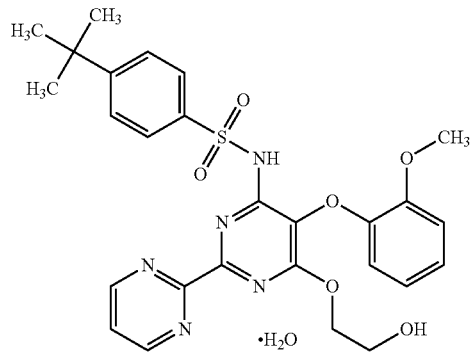

Bosentan is useful for the treatment of pulmonary arterial hypertension (PAH) to improve exercise capacity and symptoms in patients with Grade III functional status.

U.S. Pat. No. 5,292,740 describes a purification method for bosentan with column chromatography using toluene and ethyl acetate mixture, and U.S. Pat. No. 6,136,971 describes a purification method for bosentan involving drop-wise addition of water to the refluxing ethanolic solution of bosentan. However, these patents do not refer to any polymorphic form of bosentan.

WO 2008/135795 describes Form 1, Form 2, Form 3, Form 4 and an amorphous form of bosentan characterized by their XRPD, IR and DSC patterns. WO 2009/047637 describes Form A1, Form A2, Form A4 and an amorphous form of bosentan characterized by their XRPD, IR and DSC patterns and the processes for their preparation. WO 2009/093127 describes crystalline Form A5 of bosentan.

WO 2009/083739 describes anhydrous crystalline Forms B and C of bosentan and Form A of amorphous bosentan characterized by their XRPD, IR and DSC patterns. It also describes calcium and barium salts of bosentan along with the processes for their preparation.

SUMMARY OF THE INVENTION

In one general aspect, the present invention provides for crystalline Form A of bosentan potassium having an XRPD pattern, which includes interplanar spacing (d) values substantially at 3.31, 3.70, 3.73, 3.82, 4.00, 4.26, 4.44, 4.55, 4.74, 4.84, 4.96, 5.29, 5.49, 8.74, 13.78, 14.76, 15.97, 19.89, and 21.54 (Å).

Embodiments of this aspect may include one or more of the final features. For example, crystalline Form A of bosentan potassium may have an XRPD pattern substantially as depicted in FIG. 1 or the DSC pattern substantially as depicted in FIG. 3.

In another general aspect, the present invention provides for a process for preparing crystalline Form A of bosentan potassium. The process includes:
a) treating bosentan with a potassium ion source in the presence of an organic solvent or a mixture of organic solvents; and
b) isolating crystalline Form A of bosentan potassium from the mixture thereof.

In another general aspect, the present invention provides for a process for preparing crystalline Form A of bosentan potassium. The process includes:
a) treating bosentan potassium with a first organic solvent;
b) treating the mixture obtained in step a) with a second organic solvent; and
c) isolating crystalline Form A of bosentan potassium from the mixture thereof.

In another general aspect, the present invention provides for crystalline Form B of bosentan potassium having an XRPD pattern, which includes interplanar spacing (d) values substantially at 3.02, 3.11, 3.25, 3.33, 3.40, 3.44, 3.63, 3.79, 3.98, 4.04, 4.44, 4.53, 4.57, 4.73, 4.82, 5.05, 5.16, 6.03, 8.29, 10.08 and 13.29 (Å).

Embodiments of this aspect may include one or more of the following features. For example, the crystalline Form B of bosentan potassium may have an XRPD pattern substantially as depicted in FIG. 4 or the DSC pattern substantially as depicted in FIG. 6.

In another general aspect, the present invention provides for a process for preparing crystalline Form B of bosentan potassium. The process includes:
a) treating bosentan with a potassium ion source in the presence of water; and
b) isolating crystalline Form B of bosentan potassium from the mixture thereof.

In another general aspect, the present invention provides for a process for preparing crystalline Form B of bosentan potassium. The process includes:
a) treating bosentan potassium with water; and
b) isolating crystalline Form B of bosentan potassium from the mixture thereof.

In yet another general aspect, the present invention provides for crystalline Form C of bosentan sodium having an XRPD pattern, which includes interplanar spacing (d) values substantially at 2.64, 2.82, 2.88, 2.97, 3.02, 3.16, 3.22, 3.36, 3.43, 3.48, 3.68, 3.79, 3.84, 3.90, 3.95, 4.01, 4.10, 4.11, 4.22, 4.34, 4.48, 4.58, 4.66, 4.74, 4.80, 4.87, 4.97, 5.24, 5.68, 5.79, 6.29, 6.72, 6.85, 7.36, 8.90, 9.73, 10.47, 10.86, 13.70 and 14.29 (Å).

Embodiments of this aspect may include one or more of the following features. For example, the crystalline Form C of bosentan sodium may have an XRPD pattern substantially as depicted in FIG. 7 or the DSC pattern substantially as depicted in FIG. 9.

In another general aspect, the present invention provides for a process for preparing crystalline Form C of bosentan sodium. The process includes:
a) treating bosentan with a sodium ion source in the presence of an organic solvent or a mixture of organic solvents; and
b) isolating crystalline Form C of bosentan sodium from the mixture thereof.

In another general aspect, the present invention provides for a process for preparing crystalline Form C of bosentan sodium. The process includes:
a) treating bosentan sodium with an organic solvent, and
b) isolating crystalline Form C of bosentan sodium from the mixture thereof.

In another general aspect, the present invention provides for crystalline Form D of bosentan sodium having an XRPD pattern, which includes interplanar spacing (d) values substantially at 2.58, 2.65, 2.81, 2.99, 3.19, 3.29, 3.34, 3.38, 3.45, 3.58, 3.72, 3.82, 3.89, 3.95, 4.04, 4.08, 4.22, 4.39, 4.45, 4.54, 4.72, 4.77, 5.17, 5.27, 5.48, 5.86, 5.95, 7.30, 9.34, 10.05, 10.94, and 21.77 (Å).

Embodiments of this aspect may include one or more of the following features. For example, the crystalline Form D of bosentan sodium may have an XRPD pattern substantially as depicted in FIG. 10 or the DSC pattern substantially as depicted in FIG. 12.

In another general aspect, the present invention provides for a process for preparing crystalline Form D of bosentan sodium. The process includes:
a) treating bosentan with a sodium ion source in the presence of water; and
b) isolating crystalline Form D of bosentan sodium from the mixture thereof.

In another general aspect, the present invention provides for a process for preparing crystalline Form D of bosentan sodium. The process includes:
a) treating bosentan sodium with water; and
b) isolating crystalline Form D of bosentan sodium from the mixture thereof.

In another general aspect, the present invention provides for crystalline Form E of bosentan ammonium having an XRPD pattern, which includes interplanar spacing (d) values substantially at 3.45, 3.58, 3.68, 4.08, 4.19, 4.55, 4.59, 4.72, 4.96, 5.24, 5.76, 7.23 and 13.69 (Å).

Embodiments of this aspect may include one or more of the following features. For example, the crystalline Form E of bosentan ammonium may have an XRPD pattern substantially as depicted in FIG. 13 or the DSC pattern as depicted in FIG. 15.

In another general aspect, the present invention provides for a process for preparing crystalline Form E of bosentan ammonium. The process includes:
a) treating bosentan with ammonia in the presence of an organic solvent or a mixture of organic solvents; and
b) isolating crystalline Form E of bosentan ammonium from the mixture thereof.

In another general aspect, the present invention provides for crystalline Form F of bosentan ammonium having an XRPD pattern, which includes interplanar spacing (d) values substantially at 2.51, 2.61, 2.71, 2.87, 2.91, 3.08, 3.19, 3.26, 3.35, 3.39, 3.46, 3.58, 3.65, 3.76, 3.91, 3.94, 4.13, 4.17, 4.31, 4.38, 4.56, 4.66, 4.74, 4.78, 5.00, 5.32, 5.51, 5.72, 5.82, 6.72, 7.82, 9.57, and 10.63 (Å).

Embodiments of this aspect may include one or more of the following features. For example, the crystalline Form F of bosentan ammonium may have an XRPD pattern substantially as depicted in FIG. 16 or the DSC pattern as depicted in FIG. 18.

In another general aspect, the present invention provides for a process for preparing crystalline Form F of bosentan ammonium. The process includes:
a) treating bosentan ammonium with water; and
b) isolating crystalline Form F of bosentan ammonium.

In another general aspect, the present invention provides for a process for the preparation of an alkali metal or ammonium salt of bosentan. The process includes:
a) treating bosentan with an alkali metal ion source or ammonia in the presence of an organic solvent, water or a mixture thereof; and
b) isolating the alkali metal or ammonium salt of bosentan from the mixture thereof.

In yet another general aspect, the present invention provides for an alkali metal salt or ammonium salt of bosentan having a purity of about 98% or above.

In a final general aspect, the present invention provides for an alkali metal salt or ammonium salt of bosentan having a purity of about 99% or above.

BRIEF DESCRIPTION OF THE DRAWINGS

FIG. 1 depicts X-Ray Powder Diffraction (XRPD) pattern of Form A of bosentan potassium.
FIG. 1A provides the table of values for the XRPD of FIG. 1.
FIG. 2 depicts Thermal Gravimetric Analysis (TGA) of Form A of bosentan potassium.
FIG. 3 depicts Differential Scanning calorimetry (DSC) pattern of Form A of bosentan potassium.
FIG. 4 depicts the XRPD pattern of Form B of bosentan potassium.
FIG. 4A provides the table of values for the XRPD of FIG. 4.
FIG. 5 depicts the TGA of Form B of bosentan potassium.
FIG. 6 depicts the DSC pattern of Form B of bosentan potassium.
FIG. 7 depicts the XRPD pattern of Form C of bosentan sodium.
FIG. 7A provides the table of values for the XRPD of FIG. 7.
FIG. 8 depicts the TGA of Form C of bosentan sodium.
FIG. 9 depicts the DSC pattern of Form C of bosentan sodium.
FIG. 10 depicts the XRPD pattern of Form D of bosentan sodium.
FIG. 10A provides the table of values for the XRPD of FIG. 10.
FIG. 11 depicts the TGA of Form D of bosentan sodium.
FIG. 12 depicts the DSC pattern of Form D of bosentan sodium.
FIG. 13 depicts the XRPD pattern of Form E of bosentan ammonium.
FIG. 13A provides the table of values for the XRPD of FIG. 13.
FIG. 14 depicts the TGA of Form E of bosentan ammonium.
FIG. 15 depicts the DSC pattern of Form E of bosentan ammonium.
FIG. 16 depicts the XRPD pattern of Form F of bosentan ammonium.
FIG. 16A provides the table of values for the XRPD of FIG. 16.

FIG. 17 depicts the TGA of Form F of bosentan ammonium.

FIG. 18 depicts the DSC pattern of Form F of bosentan ammonium.

DETAILED DESCRIPTION OF THE INVENTION

The present invention provides for crystalline Form A of bosentan potassium. The crystalline Form A of bosentan potassium has substantially the same XRPD pattern as depicted in FIG. 1. The XRPD of crystalline Form A of bosentan potassium shows the characteristic interplanar spacing (d) values substantially at 3.31, 3.70, 3.73, 3.82, 4.00, 4.26, 4.44, 4.55, 4.74, 4.84, 4.96, 5.29, 5.49, 8.74, 13.78, 14.76, 15.97, 19.89, and 21.54 (Å). The XRPD of crystalline Form A of bosentan potassium shows the characteristic 2θ values substantially at 26.97, 24.02, 23.83, 23.26, 22.20, 20.85, 20.01, 19.49, 18.72, 18.33, 17.87, 16.74, 16.12, 10.12, 6.42, 5.99, 5.53, 4.44 or 4.10±0.2θ. The TGA of crystalline Form A of bosentan potassium has substantially the same pattern as depicted in FIG. 2 and the DSC has substantially the same pattern as depicted in FIG. 3. The DSC exhibits one melting endotherm between about 160° C. and about 170° C.

The present invention also provides a process for preparing crystalline Form A of bosentan potassium, wherein the process includes:
a) treating bosentan with a potassium ion source in the presence of an organic solvent or a mixture of organic solvents; and
b) isolating crystalline Form A of bosentan potassium from the mixture thereof.

The bosentan used as starting material may be prepared according to the methods provided in U.S. Pat. Nos. 6,136,971 and 5,292,740. The starting bosentan may be in the form of a monohydrate. The bosentan is treated with a potassium ion source in the presence of an organic solvent or a mixture of organic solvents. The organic solvent is selected from the group consisting of halogenated solvents, for example, chloroform, carbon tetrachloride, dichloromethane or ethylene dichloride; alcoholic solvents, for example, methanol, ethanol, n-propanol, n-butanol, isopropyl alcohol, n-pentanol, n-hexanol or n-octanol; ester solvents, for example, ethyl acetate, methyl acetate, propyl acetate or butyl acetate; cyclic ethers, for example, tetrahydrofuran or dioxane; aromatic hydrocarbons, for example, toluene or xylene; and aliphatic hydrocarbons, for example, n-hexane, pentane, n-heptane or n-octane.

The potassium ion source may be, for example, potassium hydroxide, potassium alkoxide or potassium carbonate. The potassium ion source may be employed in solid or solution form, for example, an alcoholic solution. The mixture may be heated to about 40° C. to about 60° C. and cooled to about 25° C. or below. The mixture may be stirred for about 0.5 hours to about 25 hours, for example, for about 1 hour to about 4 hours. The crystalline Form A of bosentan potassium is isolated from the mixture by conventional methods, for example, filtration, distillation, decantation or centrifugation or a combination thereof, and optionally washed and dried.

The present invention also provides a process for preparing crystalline Form A of bosentan potassium, wherein the process includes:
a) treating bosentan potassium with a first organic solvent;
b) treating the mixture obtained in step a) with a second organic solvent; and
c) isolating crystalline Form A of bosentan potassium from the mixture thereof.

The bosentan potassium used as starting material may be in any solid form. The bosentan potassium used as the starting material may be prepared by treating bosentan with a potassium ion source. The bosentan potassium is treated with a first organic solvent. The first organic solvent is a halogenated solvent, for example, chloroform, carbon tetrachloride, dichloromethane or ethylene dichloride; or an alcoholic solvent, for example, methanol, ethanol, n-propanol, n-butanol, isopropyl alcohol, n-pentanol, n-hexanol or n-octanol, or a mixture thereof. The mixture of bosentan potassium with the first organic solvent may be heated to about 40° C. to about 60° C. and the solvent may be partially recovered. The mixture is treated with a second organic solvent. The second organic solvent is an ester, for example, ethyl acetate, methyl acetate, propyl acetate or butyl acetate. The mixture so obtained may be cooled to about 25° C. and stirred for about 1 hour to about 50 hours. The crystalline Form A of bosentan potassium solid is isolated by conventional methods, for example, decantation, filtration, distillation or centrifugation or a combination thereof, and optionally washed and dried.

The present invention also provides for crystalline Form B of bosentan potassium. The crystalline Form B of bosentan potassium has substantially the same XRPD pattern as depicted in FIG. 4. The XRPD of crystalline Form B of bosentan potassium shows the characteristic interplanar spacing (d) values substantially at 3.02, 3.11, 3.25, 3.33, 3.40, 3.44, 3.63, 3.79, 3.98, 4.04, 4.44, 4.53, 4.57, 4.73, 4.82, 5.05, 5.16, 6.03, 8.29, 10.08 and 13.29 (Å). The XRPD of crystalline Form B of bosentan potassium shows the characteristic 2θ values substantially at 29.60, 28.72, 27.43, 26.73, 26.19, 25.88, 24.53, 23.46, 22.32, 21.99, 19.98, 19.60, 19.40, 18.76, 18.39, 17.56, 17.19, 14.69, 10.66, 8.77 and 6.65±0.2θ. The TGA of crystalline Form B of bosentan potassium has substantially the same pattern as depicted in FIG. 5 and the DSC has substantially the same pattern as depicted in FIG. 6. The DSC exhibits two melting endotherms between about 102° C. and about 112° C. and between about 285° C. and about 290° C.

The present invention also provides for a process for preparing crystalline Form B of bosentan potassium, wherein the process includes:
a) treating bosentan with a potassium ion source in the presence of water; and
b) isolating the crystalline Form B of bosentan potassium from the mixture thereof.

The bosentan used as starting material may be prepared according to the methods provided in U.S. Pat. Nos. 6,136,971 and 5,292,740. The starting bosentan may be in the form of monohydrate. The bosentan is treated with a potassium ion source in the presence of water. The mixture may be heated to about 40° C. to about 80° C. and cooled to about 25° C. or below. The potassium ion source may be, for example, potassium hydroxide or potassium carbonate. The potassium ion source may be employed in solid or solution form, for example, an aqueous solution. The mixture may be stirred for about 0.5 hours to about 25 hours, for example, for about 1 hour to about 4 hours. The crystalline Form B of bosentan potassium is isolated from the mixture by conventional methods, for example, filtration, distillation, decantation or centrifugation or a combination thereof, and optionally washed and dried.

The present invention also provides a process for preparing crystalline Form B of bosentan potassium, wherein the process includes:
a) treating bosentan potassium with water; and
b) isolating crystalline Form B of bosentan potassium from the mixture thereof.

The bosentan potassium used as the starting material may be in any solid form. The bosentan potassium used as the starting material may be prepared by treating bosentan with a potassium ion source. The bosentan potassium is treated with water. The mixture containing bosentan potassium and water may be heated to about 60° C. to about 70° C. The mixture may be cooled to about 25° C. or below and stirred for a period of about 0.5 hours to about 50 hours. The crystalline Form B of bosentan potassium may be isolated by conventional methods, for example, decantation, filtration, distillation or centrifugation or a combination thereof, and optionally washed and dried.

The present invention also provides for crystalline Form C of bosentan sodium. The crystalline Form C of bosentan sodium has substantially the same XRPD pattern as depicted in FIG. 7. The XRPD of crystalline Form C of bosentan sodium shows the characteristic interplanar spacing (d) values substantially at 2.64, 2.82, 2.88, 2.97, 3.02, 3.16, 3.22, 3.36, 3.43, 3.48, 3.68, 3.79, 3.84, 3.90, 3.95, 4.01, 4.10, 4.11, 4.22, 4.34, 4.48, 4.58, 4.66, 4.74, 4.80, 4.87, 4.97, 5.24, 5.68, 5.79, 6.29, 6.72, 6.85, 7.36, 8.90, 9.73, 10.47, 10.86, 13.70 and 14.29 (Å). The XRPD of crystalline Form C of bosentan sodium shows the characteristic 2θ values substantially at 33.97, 31.68, 31.01, 30.07, 29.58, 28.19, 27.71, 26.49, 25.92, 25.55, 24.16, 23.44, 23.12, 22.76, 22.47, 22.13, 21.69, 21.59, 21.04, 20.48, 19.82, 19.38, 19.06, 18.17, 18.47, 18.21, 17.84, 16.92, 15.59, 15.31, 14.07, 13.17, 12.92, 12.02, 9.94, 9.09, 8.45, 8.14, 6.45 and 6.18±0.2θ. The TGA of crystalline Form C of bosentan sodium has substantially the same pattern as depicted in FIG. 8 and the DSC has substantially the same pattern as depicted in FIG. 9. The DSC exhibits two melting endotherms between about 100° C. and about 115° C. and between about 180° C. and about 210° C.

The present invention also provides for a process for preparing crystalline Form C of bosentan sodium, wherein the process includes:
 a) treating bosentan with a sodium ion source in the presence of an organic solvent or a mixture of organic solvents; and
 b) isolating the crystalline Form C of bosentan sodium from the mixture thereof.

The bosentan used as starting material may be prepared according to the methods provided in U.S. Pat. Nos. 6,136,971 and 5,292,740. The starting bosentan may be in the form of a monohydrate. The bosentan is treated with a sodium ion source in the presence of an organic solvent or a mixture of organic solvents. The organic solvent is selected from the group consisting of halogenated solvents, for example, chloroform, carbon tetrachloride, dichloromethane or ethylene dichloride; alcoholic solvents, for example, methanol, ethanol, n-propanol, n-butanol, isopropyl alcohol, n-pentanol, n-hexanol or n-octanol; ester solvents, for example, ethyl acetate, methyl acetate, propyl acetate or butyl acetate; cyclic ethers, for example, tetrahydrofuran or dioxane; aromatic hydrocarbons, for example, toluene or xylene; and aliphatic hydrocarbons, for example, n-hexane, pentane, n-heptane or n-octane. The sodium ion source may be, for example, sodium hydroxide, sodium alkoxide or sodium carbonate. The sodium ion source may be employed in solid or solution form, for example, an alcoholic solution. The mixture is optionally heated to about 40° C. to about 60° C. and cooled to about 25° C. or below. The mixture may be stirred for about 0.5 hours to about 25 hours, for example, for about 1 hour to about 10 hours. The crystalline Form C of bosentan sodium is isolated from the mixture by conventional methods, for example, filtration, distillation, decantation or centrifugation or a combination thereof, and optionally washed and dried.

The present invention also provides for a process for preparing crystalline Form C of bosentan sodium, wherein the process includes:
 a) treating bosentan sodium with an organic solvent or a mixture of organic solvents; and
 b) isolating crystalline Form C of bosentan sodium from the mixture thereof.

The bosentan sodium used as starting material may be in any solid form. The bosentan sodium used as the starting material may be prepared by treating bosentan with sodium ion source. The bosentan sodium is treated with an organic solvent or a mixture of organic solvents. The organic solvent is selected from the group consisting of halogenated solvents, for example, chloroform, carbon tetrachloride, dichloromethane or ethylene dichloride; alcoholic solvents, for example, methanol, ethanol, n-propanol, n-butanol, isopropyl alcohol, n-pentanol, n-hexanol or n-octanol; ester solvents, for example, ethyl acetate, methyl acetate, propyl acetate or butyl acetate; cyclic ethers, for example, tetrahydrofuran or dioxane; aromatic hydrocarbons, for example, toluene or xylene; and aliphatic hydrocarbons, for example, n-hexane, pentane, n-heptane or n-octane. The mixture may be optionally heated from to about 40° C. to about 60° C. and the solvent may be partially recovered. The mixture may be optionally further treated with an ester solvent, for example, ethyl acetate, methyl acetate, propyl acetate or butyl acetate. The mixture may be optionally cooled to about 25° C. or below and stirred for a period of from about 1 hour to about 50 hours. The crystalline Form C of bosentan sodium is isolated by conventional means, for example decantation, filtration, distillation or centrifugation, or a combination thereof, and optionally washed and dried.

The present invention also provides for crystalline Form D of bosentan sodium. The crystalline Form D of bosentan sodium has substantially the same XRPD pattern as depicted in FIG. 10. The XRPD of crystalline Form D of bosentan sodium shows the characteristic interplanar spacing (d) values substantially at 2.58, 2.65, 2.81, 2.99, 3.19, 3.29, 3.34, 3.38, 3.45, 3.58, 3.72, 3.82, 3.89, 3.95, 4.04, 4.08, 4.22, 4.39, 4.45, 4.54, 4.72, 4.77, 5.17, 5.27, 5.48, 5.86, 5.95, 7.30, 9.34, 10.05, 10.94 and 21.77 (Å). The XRPD of Form D of bosentan sodium shows the characteristic 2θ values substantially at 34.81, 33.83, 31.81, 29.79, 28.01, 27.12, 26.66, 26.36, 25.86, 24.90, 23.92, 23.30, 22.86, 22.51, 22.03, 21.79, 21.07, 20.24, 19.94, 19.55, 18.81, 18.59, 17.16, 16.82, 16.18, 15.11, 14.89, 12.12, 9.47, 8.80, 8.09 or 4.06±0.2θ. The TGA of crystalline Form D of bosentan sodium has substantially the same pattern as depicted in FIG. 11 and the DSC has substantially the same pattern as depicted in FIG. 12. The DSC exhibits two melting endotherms between about 75° C. and about 95° C. and between about 200° C. and about 220° C.

The present invention also provides for a process of preparing crystalline Form D of bosentan sodium, wherein the process includes:
 a) treating bosentan with a sodium ion source in the presence of water; and
 b) isolating crystalline Form D of bosentan sodium from the mixture thereof.

The bosentan used as starting material may be prepared according to the methods provided in U.S. Pat. Nos. 6,136,971 and 5,292,740. The starting bosentan may be in the form of monohydrate. The bosentan is treated with a sodium ion source in the presence of water. The sodium ion source may be, for example, sodium hydroxide or sodium carbonate. The sodium ion source may be employed in solid or solution form, for example, an aqueous solution. The mixture may be heated to about 40° C. to about 80° C. and cooled to about 25° C. or below. The mixture may be stirred for about 0.5 hours to about 50 hours, for example, for about 1 hour to about 4 hours. The crystalline Form D of bosentan sodium is isolated from the mixture by conventional methods, for example, filtration, distillation, decantation or centrifugation or a combination thereof, and optionally washed and dried.

The present invention provides a process for preparing crystalline Form D of bosentan sodium, wherein the process comprises:
 a) treating bosentan sodium with water; and
 b) isolating crystalline Form D of bosentan sodium from the mixture thereof.

The bosentan sodium used as the starting material may be in any solid form. The bosentan sodium used as the starting material may be prepared by treating bosentan with a sodium ion source. The bosentan sodium is treated with water. The mixture containing bosentan sodium and water may be heated to about 50° C. to about 70° C. and cooled to about 25° C. or below. The mixture may be stirred for a period of about 0.5 hours to about 50 hours. The crystalline Form D of bosentan sodium may be isolated by conventional methods, for example, decantation, filtration, distillation or centrifugation or a combination thereof, and optionally washed and dried.

The present invention also provides for crystalline Form E of bosentan ammonium. The crystalline Form E of bosentan ammonium has substantially the same XRPD pattern as depicted in FIG. 13. The XRPD of crystalline Form E of bosentan ammonium shows the characteristic interplanar spacing (d) values substantially at 3.45, 3.58, 3.68, 4.08, 4.19, 4.55, 4.59, 4.72, 4.96, 5.24, 5.76, 7.23 and 13.69 (Å). The XRPD of Form E of bosentan ammonium shows the characteristic 2θ values substantially at 25.83, 24.84, 24.19, 21.77, 21.16, 19.50, 19.31, 18.78, 17.89, 16.91, 15.39, 12.25, and 6.45±0.2θ. The TGA of crystalline Form E of bosentan ammonium has substantially the same pattern as depicted in FIG. 14 and the DSC has substantially the same pattern as depicted in FIG. 15. The DSC exhibits two melting endotherms between about 100° C. and about 120° C. and between about 140° C. and about 165° C.

The present invention provides for a process of preparing crystalline Form E of bosentan ammonium, wherein the process includes:
 a) treating bosentan with ammonia in the presence of an organic solvent or a mixture of organic solvents; and
 b) isolating crystalline Form E of bosentan ammonium from the mixture thereof.

The bosentan used as starting material may be prepared according to the methods provided in U.S. Pat. Nos. 6,136,971 and 5,292,740. The starting bosentan may be in the form of a monohydrate. The bosentan is treated with ammonia in the presence of an organic solvent or a mixture of organic solvents. The organic solvent is selected from the group consisting of halogenated solvents, for example, chloroform, carbon tetrachloride, dichloromethane or ethylene dichloride; alcoholic solvents, for example, methanol, ethanol, n-propanol, n-butanol, isopropyl alcohol, n-pentanol, n-hexanol or n-octanol; ester solvents, for example, ethyl acetate, methyl acetate, propyl acetate or butyl acetate; cyclic ethers, for example, tetrahydrofuran or dioxane; aromatic hydrocarbons, for example, toluene or xylene; and aliphatic hydrocarbons, for example, n-hexane, pentane, n-heptane or n-octane. The ammonia may be employed in gaseous form. The mixture may be partially or completely concentrated and treated further with the organic solvent or a mixture of the organic solvents. The mixture may be stirred for about 0.5 hours to about 25 hours, for example, for about 1 hour to about 5 hours. The crystalline Form E of bosentan ammonium is isolated from the mixture by conventional methods, for example, filtration, distillation, decantation or centrifugation or a combination thereof, and optionally washed and dried.

The present invention also provides for crystalline Form F of bosentan ammonium. The crystalline Form F of bosentan ammonium has substantially the same XRPD pattern as depicted in FIG. 16. The XRPD of crystalline Form F of bosentan ammonium shows characteristic interplanar spacing (d) values substantially at 2.51, 2.61, 2.71, 2.87, 2.91, 3.08, 3.19, 3.26, 3.35, 3.39, 3.46, 3.58, 3.65, 3.76, 3.91, 3.94, 4.13, 4.17, 4.31, 4.38, 4.56, 4.66, 4.74, 4.78, 5.00, 5.32, 5.51, 5.72, 5.82, 6.72, 7.82, 9.57 and 10.63 (Å). The XRPD of crystalline Form F of bosentan ammonium shows the characteristic 2θ values substantially at 35.84, 33.07, 31.21, 30.73, 29.01, 27.96, 27.39, 26.63, 26.31, 25.75, 24.85, 24.37, 23.69, 22.73, 22.59, 21.53, 21.30, 20.59, 20.27, 19.46, 19.06, 18.71, 18.57, 17.73, 16.68, 16.09, 15.49, 15.23, 13.18, 11.31, 9.24 and 8.32±0.2θ. The TGA of crystalline Form F of bosentan ammonium has substantially the same pattern as depicted in FIG. 17 and the DSC has substantially the same pattern as depicted in FIG. 18. The DSC exhibits a melting endotherm between about 160° C. and about 170° C.

The present invention also provides for a process of preparing crystalline Form F of bosentan ammonium, wherein the process includes:
 a) treating bosentan ammonium with water; and
 b) isolating crystalline Form F of bosentan ammonium from the mixture thereof.

The bosentan ammonium used as the starting material may be in any solid form. The bosentan ammonium used as the starting material may be prepared by treating bosentan with ammonia. The bosentan ammonium is treated with water. The mixture containing bosentan potassium and water may be heated to about 60° C. to about 80° C. The mixture may be stirred for a period of about 0.5 hours to about 50 hours. The crystalline Form F of bosentan ammonium may be isolated by conventional methods, for example, decantation, filtration, distillation or centrifugation or a combination thereof, and optionally washed and dried.

The present invention also provides for a process of the preparation of an alkali metal or ammonium salt of bosentan, wherein the process includes:
 a) treating bosentan with an alkali metal ion source or ammonia in the presence of an organic solvent, water or a mixture thereof; and
 b) isolating an alkali metal or ammonium salt of bosentan from the mixture thereof.

The bosentan used as starting material may be prepared according to the methods provided in for example U.S. Pat. Nos. 6,136,971 and 5,292,740. The bosentan may be in the form of monohydrate. The bosentan is treated with an alkali metal ion source or ammonia in the presence of an organic solvent, water, or a mixture thereof. The organic solvent is selected from the group consisting of halogenated solvents, for example, chloroform, carbon tetrachloride, dichloromethane or ethylene dichloride; alcoholic solvents, for example, methanol, ethanol, n-propanol, n-butanol, isopropyl alcohol, n-pentanol, n-hexanol or n-octanol; ester solvents, for example, ethyl acetate, methyl acetate, propyl acetate or butyl acetate; cyclic ethers, for example, tetrahydrofuran or dioxane; aromatic hydrocarbons, for example, toluene or xylene; and aliphatic hydrocarbons, for example, n-hexane, pentane, n-heptane or n-octane.

The alkali metal ion source is selected from the group comprising of alkali metal hydroxides, for example, sodium hydroxide, potassium hydroxide or lithium hydroxide; alkali metal alkoxides, for example, lithium methoxide, potassium methoxide, sodium methoxide, sodium ethoxide or potassium ethoxide; and alkali metal carbonates, for example, sodium carbonate or potassium carbonate. The alkali metal ion source may be employed in solid form or in solution form.

The ammonia may be employed in gaseous form or in solution form. The mixture may be heated from about 40° C. to about reflux temperature of the solvent. The solvent may be partially or completely recovered. The solvent recovery may be followed by the further addition of the organic solvent or water. The reaction mixture may be cooled 25° C. or below. The reaction mixture may be stirred for a period of about 1 hour to about 50 hours. The alkali metal or ammonium salt of bosentan obtained is isolated by conventional methods, for example decantation, filtration, distillation or centrifugation or a combination thereof.

The alkali metal or ammonium salt of bosentan so obtained may be further purified by treating with an organic solvent or a mixture of organic solvents, or water. The organic solvent is selected from the group consisting of halogenated solvents, for example, chloroform, carbon tetrachloride, dichloromethane or ethylene dichloride; alcoholic solvents, for example, methanol, ethanol, n-propanol, n-butanol, isopropyl alcohol, n-pentanol, n-hexanol or n-octanol; ester solvents, for example, ethyl acetate, methyl acetate, propyl acetate or butyl acetate; cyclic ethers, for example, tetrahydrofuran or dioxane; aromatic hydrocarbons, for example, toluene or xylene; and aliphatic hydrocarbons, for example, n-hexane, pentane, n-heptane or n-octane. The alkali metal or ammonium salt of bosentan, so obtained, has a purity of about 97% or above, for example, about 98% or above, or about 99% or above. The pure alkali metal or ammonium salt of bosentan may be obtained as crystalline forms, for example, Form A and Form B of bosentan potassium, Form C and Form D of bosentan sodium, and Form E and Form F of bosentan ammonium. The pure alkali metal or ammonium salt of bosentan so obtained may be further converted into bosentan by treating with an organic or inorganic acid, for example, sulfuric acid, hydrochloric acid, phosphoric acid, or nitric acid.

The present invention also provides for a pharmaceutical composition that includes an alkali metal or ammonium salt of bosentan, and a carrier. The alkali metal or ammonium salt of bosentan may be in crystalline forms, for example, Form A and Form B of bosentan potassium, Form C and Form D of bosentan sodium, and Form E and Form F of bosentan ammonium.

The High performance liquid chromatography (HPLC) was performed using Intertsil ODS-3V, 5_tm as column, acetonitrile and buffer solution such as orthophosphoric acid (50:50) as mobile phase, and a temperature of 5° C.

XRPD of the samples were determined using X-Ray diffractometer, Rigaku Corporation, RU-H3R, Goniometer CN2155A3, X-Ray tube with Cu target anode, Power: 40 KV, 100 Ma, Scanning speed: 2 deg/min step: 0.02 deg, Wave length: 1.5406 Å.

The TGA and DSC patterns were recorded using TA instruments-Q500 and Mettler Toledo DSC 821e, respectively.

While the present invention has been described in terms of its specific embodiments, certain modifications and equivalents will be apparent to those skilled in the art and are intended to be included within the scope of the present invention.

EXAMPLES

Example 1

Preparation of Form A of the Bosentan Potassium

Step 1: Preparation of Bosentan
Sodium hydroxide (26.66 g), ethylene glycol (400 mL), tetrabutylammonium bromide (10 g), 4-tert-butyl-N-[6-chloro-5-(2-methoxyphenoxy)-2,2'-bipyrimidin-4-yl]benzenesulfonamide (100 g) and dimethylsulphoxide (400 mL) were mixed together at 25° C. The reaction mixture was heated to 60° C. to 65° C. and the mixture was stirred for 12-14 hours at 60° C. to 65° C. The reaction mixture was cooled to 25° C. followed by the addition of dichloromethane (600 mL) and de-ionized water (1000 mL). The pH of the mixture was adjusted to 2 to 3 with concentrated hydrochloric acid and the mixture was stirred for 10 minutes. The organic layer of the reaction mixture was separated. The aqueous layer was extracted with dichloromethane (200 mL). Both the organic layers were combined, washed with de-ionized water (500 mL) and the solvent was recovered. The residue was dried under vacuum at 40° C. to 50° C. to obtain bosentan.
Weight: 89 g
Chromatographic purity: 96.29%

Step 2: Preparation of Bosentan Potassium
The bosentan, as obtained in Step 1, was dissolved in methanol (200 mL) at 40° C. to 50° C. The mixture was cooled to about 20° C. to 25° C. Dichloromethane (50 mL), ethyl acetate (800 mL) and potassium hydroxide (12.8 g) were added to the mixture and a clear solution was obtained. The solution was stirred for 3 hours at 20° C. to 25° C. and the solid obtained was filtered and dried to obtain bosentan potassium.
Weight: 85 g
Chromatographic purity: 98.96%

Step 3: Preparation of Form A of the Bosentan Potassium
Methanol (200 mL) and dichloromethane (200 ml) were added to the bosentan potassium as obtained in Step 2. The mixture was heated to 50° C. to 55° C. The mixture was stirred for 20 minutes at the same temperature and dichloromethane (~150 mL) was recovered at atmospheric pressure at 40° C. to 55° C. Ethyl acetate (800 mL) was added to the residue at 50° C. to 55° C. The reaction mixture was cooled to 20° C. to 25° C., stirred for 3 hours, filtered and washed with a mixture of methanol (20 mL) and ethyl acetate (80 mL). The solid obtained was dried under vacuum at 55° C. to 60° C. until the loss on drying was not more than 2.0% w/w to obtain the title compound.
Weight: 80 g
Chromatographic purity: 99.69%

Example 2

Preparation of Form A of the Bosentan Potassium

Potassium hydroxide (0.45 g) was added to a mixture of bosentan monohydrate (3.5 g), methanol (7 mL), dichloromethane (1.75 mL) and ethyl acetate (28 mL). The reaction mixture was stirred for 3 hours at 20° C. to 25° C. and the solid obtained was filtered. Methanol (7 mL) and dichloromethane (7 mL) were added to the solid. The mixture was heated to 40° C. to 45° C. The reaction mixture was stirred for 15 minutes at same temperature and dichloromethane (~5 mL) was recovered at atmospheric pressure at 40° C. to 50° C. Ethyl acetate (28 mL) was added at 50° C. to 55° C. to the reaction mixture, cooled to 20° C. to 25° C. and stirred for 3 hours. The solid obtained was filtered, washed with a mixture of methanol (0.7 mL) and ethyl acetate (2.8 mL) and dried under vacuum at 55° C. to 60° C. to obtain the title compound.
Weight: 2.5 g
Chromatographic purity: 99.76%

Example 3

Preparation of Form A of the Bosentan Potassium

Potassium methoxide (0.59 g) was added to a mixture of bosentan monohydrate (4 g) in methanol (6 mL), dichloromethane (1.75 mL) and ethyl acetate (24 mL). The reaction mixture was stirred for 30 minutes at 55° C. to 60° C. The reaction mixture was cooled to 25° C. and stirred for 2 hours at the same temperature. The solid obtained was filtered, washed with a mixture of methanol (0.8 mL) and ethyl acetate (3.2 mL) and dried under vacuum at 55° C. to 60° C. to obtain the title compound.
Weight: 3.5 g
Chromatographic purity: 98.76%

Example 4

Preparation of Form B of the Bosentan Potassium

Bosentan potassium (3 g) was dissolved in de-ionized water (18 mL) by heating to 65° C. to 70° C., stirred for 2 hours at 65° C. to 70° C., cooled and further stirred for 1 hour at 25° C. to 20° C. The solid was filtered and washed with de-ionized water (10 mL). The wet material obtained was dried under vacuum at 40° C. to 45° C. to obtain the title compound.
Weight: 2.4 g
Chromatographic purity: 99.7%

Example 5

Preparation of Form B of the Bosentan Potassium

Step 1: Preparation of Bosentan
Sodium hydroxide (6.65 g), ethylene glycol (100 mL), tetrabutylammonium bromide (2.5 g), 4-tert-butyl-N-[6-chloro-5-(2-methoxyphenoxy)-2,2'-bipyrimidin-4-yl]benzenesulfonamide (25 g) and dimethylsulphoxide (100 mL) were mixed and heated to 60° C. to 65° C. The reaction mixture was stirred for 12 hours to 14 hours at 60° C. to 65° C. The reaction mixture was cooled to 25° C. followed by the addition of dichloromethane (150 mL) and de-ionized water (250 mL). The pH of the mixture was adjusted to 2 to 3 with concentrated hydrochloric acid. The mixture was stirred for 10 minutes and the organic layer was separated. The aqueous layer was extracted with dichloromethane (50 mL). Both the organic layers were combined and washed with deionized water (125 mL). The dichloromethane was recovered and dried under vacuum at 40° C. to 50° C. to obtain the title compound.
Weight of residue: 22.5 g
Chromatographic purity: 96.12%
Step 2: Preparation of Bosentan Potassium
Bosentan (residue as obtained in Step 1; 5 g), de-ionized water (15 mL) and potassium hydroxide (0.64 g) were mixed. The reaction mixture was heated to 55° C. and stirred for 15 minutes at 55° C. The reaction mixture was cooled to 25° C. to 20° C. and stirred over night. The solid was filtered and washed with de-ionized water (5 mL). The wet material obtained was dried under vacuum at 50° C. to 55° C. to obtain the title compound.
Weight: 3.99 g
Chromatographic purity: 98.14%

Example 6

Preparation of Form B of the Bosentan Potassium

Bosentan potassium (5 g) was mixed with de-ionized water (25 mL) and the mixture was heated to 65° C. to 70° C. The reaction mixture was stirred for 2 hours (solid started separating after 30 minutes). The solid was filtered, washed with de-ionized water (10 mL) and dried under vacuum at 40° C. to 45° C. to obtain the title compound.
Weight: 3.8 g
Chromatographic purity: 98.76%

Example 7

Preparation of Form C of the Bosentan Sodium

Step 1: Preparation of Bosentan Sodium
Sodium hydroxide (0.44 g) was added to a mixture of bosentan (5 g) in methanol (10 mL), dichloromethane (2.5 mL) and ethyl acetate (40 mL). The reaction mixture was stirred for 3.5 hours at 20° C. to 25° C. and the solid was filtered to obtain the title compound.
Chromatographic purity: 98.06%
Step 2: Preparation of Form C of Bosentan Sodium
Methanol (10 mL) and dichloromethane (10 mL) were added to the solid as obtained in Step 1. The mixture was heated to 50° C. to 55° C. and stirred for 20 minutes at 50° C. to 55° C. Dichloromethane (~6 mL) was recovered from the reaction mixture at atmospheric pressure at 40° C. to 55° C. and ethyl acetate (40 mL) was added to the residue at 50° C. to 55° C. The reaction mixture was cooled to 20° C. to 25° C. and stirred for 3 hours. The solid obtained was filtered, washed with a mixture of methanol (1 mL) and ethyl acetate (4 mL) and dried under vacuum at 55° C. to 60° C.
Weight: 2.3 g
Chromatographic purity: 99.71%

Example 8

Preparation of Form C of the Bosentan Sodium

Ethyl acetate (30 mL) was added to the solid as obtained in Step-1 and the mixture was stirred for 3 hours at 25° C. The solid so obtained was filtered, washed with ethyl acetate (30 mL) and dried under vacuum at 45° C. to 50° C. to obtain the title compound.
Weight: 1.8 g
Chromatographic purity: 95.74%

Example 9

Preparation of Form-C of the Bosentan Sodium

Sodium methoxide solution (30% methanolic solution) was added to a mixture of bosentan monohydrate (10 g) in methanol (20 mL) and ethyl acetate (80 mL). The reaction mixture was stirred for 3 hours and the solid was filtered, washed with ethyl acetate (20 mL) and dried at hot air oven at 50° C. to 55° C. to obtain the title compound.
Weight: 8.7 g

Example 10

Preparation of Form C of the Bosentan Sodium

Sodium methoxide solution (30% methanolic solution; 3.9 mL) was added to a mixture of bosentan monohydrate (5 g) in methanol (15 mL). Ethyl acetate (80 mL) was added to the reaction mixture. The reaction mixture was heated to 55° C. and stirred for 30 minutes at 55° C. The reaction mixture was cooled to 25° C. The reaction mixture was stirred for 1.5 hours and the solid was filtered at 10° C. to 15° C., washed with a mixture of ethyl acetate (4 mL) and methanol (1 mL). The wet material obtained was dried at hot air oven at 50° C. to 55° C. to obtain the title compound.
Weight: 3.1 g

Example 11

Preparation of Form D of the Bosentan Sodium

Sodium hydroxide powder (0.43 g) was added to a mixture of bosentan (5 g) in deionized water (20 mL) and the resultant mixture was heated to 55° C. The reaction mixture was stirred for 15 minutes at the same temperature. The reaction mixture was cooled to 25° C. and the mixture was further stirred for 5 hours. The solid obtained was filtered, washed with de-ionized water and dried in air for 12 hours at 55° C. to 60° C. to obtain the title compound.
Weight: 3.57 g
Chromatographic purity: 96.55%

Example 12

Preparation of Form D of the Bosentan Sodium

Sodium pieces (2.19 g) were added slowly to ethylene glycol (55 mL) at 50° C. and cooled to room temperature. 4-tert-butyl-N-[6-chloro-5-(2-methoxyphenoxy)-2,2'-bipyrimidin-4-yl]benzenesulfonamide (5 g) was added to the mixture and heated to 98° C. to 100° C. The reaction mixture was stirred for 1 hour and cooled to 25° C. The cooled reaction mixture was poured slowly into ice of de-ionized water and stirred for 4 hours at 25° C. The solid was filtered and dried under vacuum for overnight at 25° C. De-ionized water (30 mL) was added to the solid and the reaction mixture was heated to 50° C. for 10 minutes. The reaction mixture was further stirred for 3 hours at 25° C. The solid obtained was filtered, washed with de-ionized water (10 mL) and dried under vacuum at 45° C. to 50° C. to obtain the title compound.
Chromatographic purity: 98.65%
Weight: 4.3 g

Example 13

Preparation of Form D of the Bosentan Sodium

A mixture of bosentan (2 g) in de-ionized water (24 mL) was heated to 50° C. followed by the addition of sodium hydroxide (0.175 g). The reaction mixture was stirred for 3.5 hours at the same temperature and the solid was filtered, washed with de-ionized water (6 mL) and dried under hot air oven at 55° C. to 60° C. to obtain the title compound.
Weight: 1.48 g

Example 14

Preparation of Form D of the Bosentan Sodium

A mixture of bosentan sodium (2 g) in de-ionized water (24 mL) was heated to 55° C. and stirred for 15 minutes to 20 minutes at the 55° C. The reaction mixture was cooled to 25° C. and stirred for over night. The solid so obtained was filtered, washed with de-ionized water de-ionized water (6 mL) and dried under air oven at 55° C. to 60° C.
Weight: 1.75 g

Example 15

Preparation of Form E of the Bosentan Ammonium

Step 1: Preparation of Bosentan
A mixture of sodium hydroxide (2.66 g), ethylene glycol (60 mL), tetrabutylammonium bromide (1 g) and 4-tert-butyl-N-[6-chloro-5-(2-methoxyphenoxy)-2,2'-bipyrimidin-4-yl]benzenesulfonamide (10 g) was heated to 95° C. to 100° C. and the reaction mixture was stirred for 4 hours at 95° C. to 100° C. The mixture was cooled to 25° C. followed by the addition of dichloromethane (40 mL) and de-ionized water (180 mL). The pH of the reaction mixture was adjusted to 2 to 3 with concentrated hydrochloric acid. The reaction mixture was stirred for 10 minutes and the organic layer was separated. The aqueous layer was extracted with dichloromethane (10 mL). Both the organic layers were combined and washed with de-ionized water (50 mL). The dichloromethane was recovered under vacuum at 40° C. to 50° C. to obtain the title compound.

Step 2: Preparation of Form E of Bosentan Ammonium
Ammonia gas was passed for 15 minutes to a mixture of the residue as obtained in Step 1 in ethyl acetate (100 mL). The reaction mixture was stirred for 1 hour and the ethyl acetate was recovered under vacuum at 50° C. to obtain the residue. The residue was mixed with a solvent mixture of methanol (20 mL) and dichloromethane (4 mL) to obtain a solution and ethyl acetate (80 mL) was added to the solution to precipitate the solid. The resultant mixture was stirred for 4 hours and the solid obtained was filtered, washed with a mixture of methanol (4 mL) and ethyl acetate (80mL) and dried under vacuum at 55° C. to 60° C. for 12 hours to obtain the title compound.
Weight: 6.55 g
Chromatographic purity: 99.12%

Example 16

Preparation of Form F of the Bosentan Ammonium

A mixture of bosentan ammonium (4 g) in de-ionized water (20 mL) was heated to 70° C. to obtain a clear solution. The reaction mixture was stirred for 2 hours. The solid obtained was filtered, washed with de-ionized water (4 mL) at 40° C. to 45° C. and dried at hot air oven at 60° C. to 65° C.
Weight: 1.29 g
Chromatographic purity: 99.60%

Example 17

Preparation of Bosentan Sodium from Bosentan

A mixture of bosentan monohydrate (10 g) in de-ionized water (120 mL) was heated to 50° C. and aqueous solution of sodium hydroxide (0.875 g of sodium hydroxide dissolved in 4 mL of de-ionized water) was added to the mixture. The resultant mixture was stirred for 1.5 hours and cooled to 20° C. to 25° C. The mixture was stirred for further 0.5 hours. The solid was filtered, washed with de-ionized water and dried for 12 hours at 40° C. to 45° C. to obtain the title compound.

Example 18

Preparation of Bosentan Potassium

Sodium hydroxide (266 g), ethylene glycol (6L), tetrabutylammonium bromide (100 g), 4-tert-butyl-N-[6-chloro-5-(2-methoxyphenoxy)-2,2'-bipyrimidin-4-yl]benzenesulfonamide (1 kg) and dimethylsulphoxide (100 mL) were mixed at 25° C. and the mixture was heated to 90° C. to 100° C. The reaction mixture was cooled to 25° C. followed by the addition of dichloromethane (4L) and de-ionized water (18 L). The pH of the mixture was adjusted to 2 to 3 with concentrated hydrochloric acid and the mixture was stirred for 10 minutes. The organic layer was separated. The aqueous layer was extracted with dichloromethane (1 L). Both the organic layers were combined and washed with de-ionized water (5 L). Dichloromethane was recovered and dried under vacuum at 40° C. to 50° C. Methanol (1.5 L) and potassium methoxide (146.3 g) were added to the residue so obtained. The reaction mixture was heated to 40° C. to 50° C. and the mixture was stirred for 15 minutes at 40° C. to 50° C. Ethyl acetate (6 L) was added to the mixture and the mixture was heated and stirred at 55° C. to 60° C. The reaction mixture was cooled to 25° C. and stirred for 2 hours. The solid obtained was filtered, washed with methanol (0.2 L) and ethyl acetate (0.8 L) and dried at hot air oven at 45° C. to 50° C. to obtain the title compound.
Weight: 0.9 g
Chromatographic purity: 96.65%

We claim:

1. Crystalline Form A of bosentan potassium having an XRPD pattern comprising interplanar spacing (d) values substantially at 3.31, 3.70, 3.73, 3.82, 4.00, 4.26, 4.44, 4.55, 4.74, 4.84, 4.96, 5.29, 5.49, 8.74, 13.78, 14.76, 15.97, 19.89, and 21.54 (Å).

2. Crystalline Form A of bosentan potassium having an XRPD pattern substantially as depicted in FIG. 1 or the DSC pattern substantially as depicted in FIG. 3.

3. A process for preparing crystalline Form A of bosentan potassium, wherein the process comprises:
   a) treating bosentan with a potassium ion source in the presence of an organic solvent or a mixture of organic solvents; and
   b) isolating crystalline Form A of bosentan potassium from the mixture thereof.

4. A process for preparing crystalline Form A of bosentan potassium, wherein the process comprises:
   a) treating bosentan potassium with a first organic solvent;
   b) treating the mixture obtained in step a) with a second organic solvent; and
   c) isolating crystalline Form A of bosentan potassium from the mixture thereof.

5. Crystalline Form A of bosentan potassium prepared according to claim 3 or 4, having a purity of about 98% or above.

6. Crystalline Form A of bosentan potassium prepared according to claim 3 or 4, having a purity of about 99% or above.

* * * * *